(12) United States Patent
Rehkemper et al.

(10) Patent No.: US 8,348,912 B2
(45) Date of Patent: Jan. 8, 2013

(54) EYE DROPPER ALIGNMENT APPARATUS AND METHOD FOR USING SAME

(75) Inventors: Jeffrey Rehkemper, Chicago, IL (US); David T. Tse, Weston, FL (US); Steven Rehkemper, Chicago, IL (US); Brad D. Simons, Palm Beach Gardens, FL (US); Jay Tapper, Wayne, PA (US)

(73) Assignee: Anakin LLC, Palm Beach Gardens, FL (US)

( * ) Notice: Subject to any disclaimer, the term of this patent is extended or adjusted under 35 U.S.C. 154(b) by 362 days.

(21) Appl. No.: 12/608,812

(22) Filed: Oct. 29, 2009

(65) Prior Publication Data

US 2011/0098664 A1 Apr. 28, 2011

Related U.S. Application Data

(60) Provisional application No. 61/254,093, filed on Oct. 22, 2009.

(51) Int. Cl.
*A61M 35/00* (2006.01)
(52) U.S. Cl. .......................... 604/302; 604/294
(58) Field of Classification Search ........... 604/294–302
See application file for complete search history.

(56) References Cited

U.S. PATENT DOCUMENTS

| | | | |
|---|---|---|---|
| 1,285,177 A * | 11/1918 | Hochstein | 359/481 |
| 1,789,937 A * | 1/1931 | Curran | 351/63 |
| 2,086,734 A * | 7/1937 | Nerney | 351/65 |
| 2,210,507 A * | 8/1940 | Spill | 351/116 |
| 2,676,592 A | 4/1954 | Wood | |
| 2,722,216 A * | 11/1955 | Robbins | 604/302 |
| 3,058,466 A | 10/1962 | Routsong | |
| 3,233,956 A * | 2/1966 | De Angelis | 351/130 |
| 3,446,209 A | 5/1969 | Macha | |
| 3,521,636 A | 7/1970 | Mahoney et al. | |
| 3,598,121 A * | 8/1971 | Lelicoff | 604/302 |
| 3,934,590 A | 1/1976 | Campagna et al. | |
| 4,002,168 A * | 1/1977 | Petterson | 604/298 |
| 4,085,750 A * | 4/1978 | Bosshold | 604/302 |
| D249,709 S * | 9/1978 | Trovinger | D24/127 |
| 4,113,365 A * | 9/1978 | Koketsu | 351/128 |
| 4,134,403 A * | 1/1979 | Johnsen et al. | 604/302 |
| 4,183,355 A | 1/1980 | Meckler | |
| 4,257,417 A | 3/1981 | Gibilisco | |
| 4,280,758 A * | 7/1981 | Flader et al. | 351/55 |
| 4,344,430 A * | 8/1982 | Astrove | 604/300 |
| 4,386,608 A * | 6/1983 | Ehrlich | 604/298 |
| 4,392,590 A * | 7/1983 | Hofmann-Igl | 222/174 |
| 4,468,103 A * | 8/1984 | Meckler | 351/158 |
| 4,471,890 A * | 9/1984 | Dougherty | 222/190 |
| 4,531,944 A * | 7/1985 | Bechtle | 604/302 |

(Continued)

*Primary Examiner* — Jackie Ho
*Assistant Examiner* — Paula Craig
(74) *Attorney, Agent, or Firm* — Fay Sharpe LLP

(57) ABSTRACT

The present application discloses a new and novel system and apparatus for improving the accuracy with which a person may apply eye drops to their own eye. The apparatus holds a bottle of eye drops at a fixed and certain distance above the eye, beside the nose, and below the forehead brow such that the user may easily apply eye drops consistently to one particular portion of their own eye. The apparatus sits on the nasion of the nose using a nasal bridge device and also rests on two pillars that are placed on the user's forehead. Used in such a manner, the apparatus facilitates one-handed eye drop application, facilitates both non-visual alignment and oblique alignment, and reduces reflective blinking.

31 Claims, 19 Drawing Sheets

U.S. PATENT DOCUMENTS

| | | | | |
|---|---|---|---|---|
| 4,543,096 A * | 9/1985 | Keene | | 604/300 |
| 4,550,866 A * | 11/1985 | Moore | | 222/420 |
| 4,573,982 A * | 3/1986 | Forbes et al. | | 604/300 |
| 4,685,906 A * | 8/1987 | Murphy | | 604/300 |
| 4,733,802 A * | 3/1988 | Sheldon | | 604/302 |
| 4,792,334 A * | 12/1988 | Py | | 604/301 |
| 4,834,727 A * | 5/1989 | Cope | | 604/300 |
| 4,986,649 A * | 1/1991 | Smith | | 351/130 |
| 5,133,702 A | 7/1992 | Py | | 604/302 |
| 5,159,359 A * | 10/1992 | Pauly et al. | | 351/128 |
| 5,171,306 A * | 12/1992 | Vo | | 604/295 |
| 5,221,027 A * | 6/1993 | Gibilsco | | 222/420 |
| 5,255,024 A * | 10/1993 | Jensen | | 351/158 |
| 5,569,224 A * | 10/1996 | Michalos | | 604/300 |
| 5,578,020 A * | 11/1996 | Mosley | | 604/295 |
| 5,583,586 A * | 12/1996 | Evans | | 351/130 |
| 5,611,788 A * | 3/1997 | Marchment | | 604/295 |
| 5,713,495 A * | 2/1998 | Menard | | 222/212 |
| 5,795,342 A * | 8/1998 | Shapiro et al. | | 604/300 |
| 5,810,794 A * | 9/1998 | Peplinski | | 604/295 |
| 5,836,927 A * | 11/1998 | Fried | | 604/300 |
| 6,010,488 A * | 1/2000 | Deas | | 604/295 |
| 6,090,027 A * | 7/2000 | Brinkman | | 493/54 |
| 6,227,371 B1 * | 5/2001 | Song | | 206/534 |
| 6,371,945 B1 * | 4/2002 | Sherman | | 604/302 |
| 6,595,970 B1 | 7/2003 | Davidian | | |
| 6,601,955 B1 * | 8/2003 | Le Van Meautte | | 351/136 |
| 7,235,065 B1 | 6/2007 | Sorensen | | |
| 7,309,329 B2 | 12/2007 | Cress | | |
| 7,325,708 B2 | 2/2008 | Barber | | |
| 7,635,070 B2 * | 12/2009 | Cohen et al. | | 222/162 |
| 8,206,362 B1 * | 6/2012 | Crosswell, Jr. | | 604/294 |
| 2003/0019879 A1 * | 1/2003 | Hubicki | | 221/15 |
| 2009/0082739 A1 * | 3/2009 | Cress | | 604/298 |
| 2009/0207373 A1 * | 8/2009 | Stinson | | 351/158 |
| 2009/0259204 A1 * | 10/2009 | Galdeti et al. | | 604/302 |
| 2010/0174248 A1 * | 7/2010 | Wu | | 604/302 |
| 2011/0118678 A1 * | 5/2011 | Rehkemper et al. | | 604/290 |

* cited by examiner

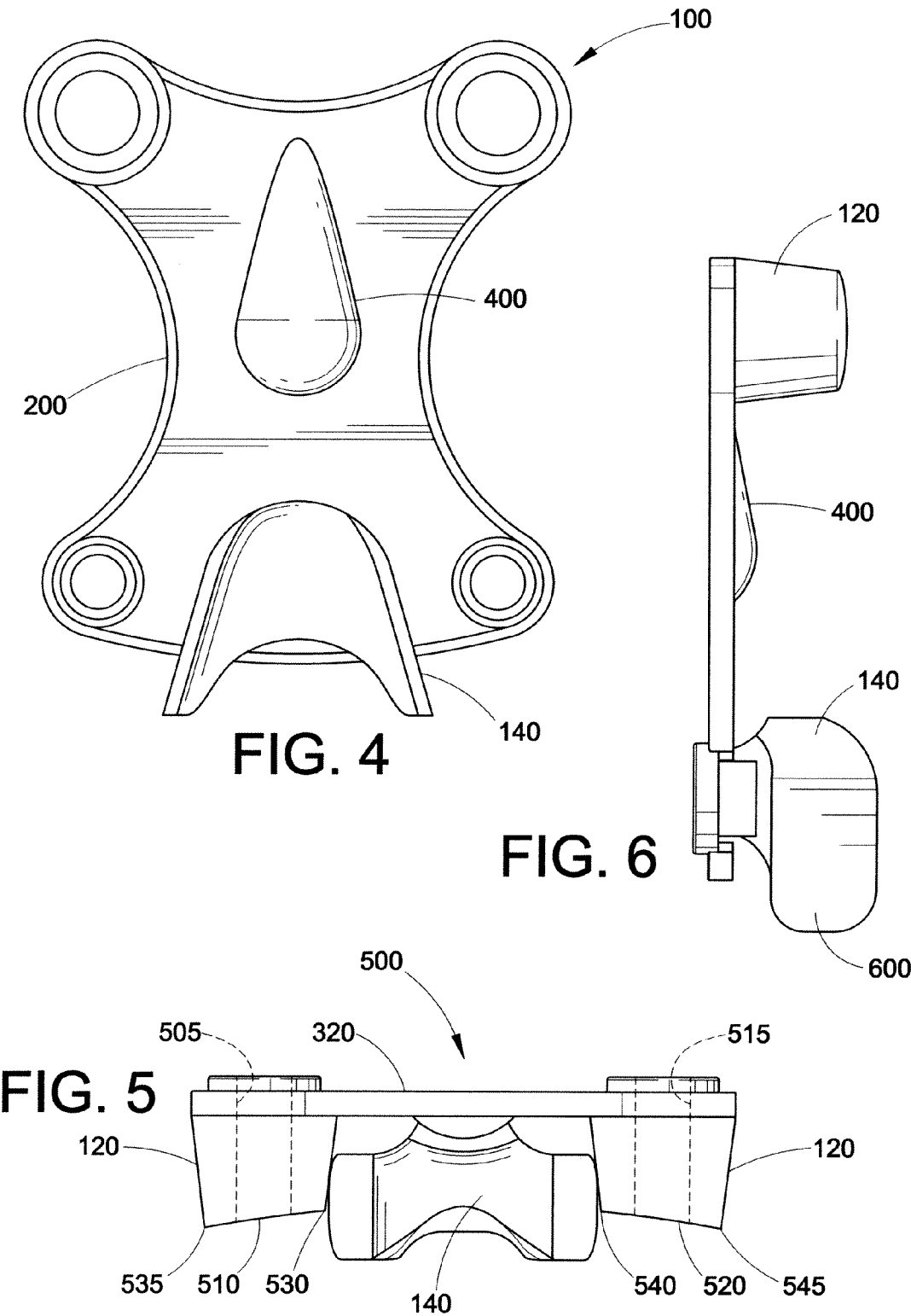

EYE DROPPER ALIGNMENT APPARATUS AND METHOD FOR USING SAME

This application claims the priority benefit of U.S. application Ser. No. 61/254,093, filed Oct. 22, 2009, the disclosure of which is incorporated herein by reference in its entirety.

FIELD

The present application provides a placement, stabilization, locating and positioning device for aligning an eye dropper, and a method for improving eye drop application using the device. The device facilitates an alignment wherein the eye drop bottle and bottom of an eye drop supply are disposed relative to a selected eye location, so that the eye drops are applied off of a visual axis drawn from the retina and through the center of the pupil. This enables both one-handed and two-handed dispensing of eye drops from the eye dropper in a manner that facilitates the non-visual alignment of an eye drop device and precludes reflexive blinking by assuring the selected alignment between the eye dropper and the eye, freeing the user from adjusting alignment and allowing the user to focus exclusively on dispensing the liquid from the eye dropper. Dual alignment wells correspond to both eyes so that a single placement of the device provides an alignment without having to reposition the device for each eye. By optimizing eye drop delivery, this device will minimize medication wastage. Contamination is avoided by shielding the eye dropper nozzle from a user's eyes and eyelashes.

BACKGROUND

Currently in the art there is a need for an eye dropper application apparatus which automatically locates an eye drop dispenser and provides stability in all three directional axes of movement; up and down the height of the eye, side to side over the width of the eye and in and out over and above the surface of the eye.

Presently in the art, apparatus using a nasal bridge saddle as a support do not provide for control about all three axes, are not particularly safe and lack the ability to accommodate both eyes.

Furthermore, there is no apparatus that provides a safer and more functionally reliable device that will preclude reflexive blinking before a drop makes contact with the eye by a user.

Reflexive blinking is influenced by visual clues and tactile sensation. If an object suddenly flies toward the eye, the eyelids will reflexively close at high speed and the head flinches—a reflex to a visual threat without any volitional control. On the other hand, if a blast of air from a jet hits the eye, the eye will reflexively blink even though it cannot see the air coming but the cornea feels the air because of tactile sensation. The design of an eye drop delivery system should be aimed at minimizing contributory factors to reflexive blinking. The user should not see the drop coming and sensation should be minimal upon eye drop contact with the eye. By not seeing the approaching eye drop, the fear of a pending strike is eliminated and thus minimizing reflexive blinking. When the eye drop does make contact with a much less sensitive caruncle, the anxiety for future application is removed, thus enhancing medication compliance.

Gibilsco (U.S. Pat. No. 4,257,417) exists in the art as a nose supported eye dropper holder. However, this apparatus only holds the bottle stable in a side-to-side direction. The holder does not produce any resistance to motion in a towards and away from the eye axis of motion, also called height precision locking. The motion of the eye dropper moving in such a manner may lead to the eye being impacted by the eye dropper and such an impact may be a source of infection or may scratch the surface of the eye. Furthermore, Gibilsco does not contain any discernable means by which up and down motion across the height of the eye may be presented, also called a stability locking mechanism. The lack of up and down stability, combined with the lack of in and out stability could even result in lack of accuracy in the side to side eye direction, as the combination of pulling the eye dropper too high up could also overshoot the iris.

Wood (U.S. Pat. No. 2,676,592) exists in the art as a nose support guide for eye droppers. However, this apparatus only positions the eye dropper over the user's eye and prevents motion only in a side-to-side axis. There is no element within this device that stops the eye dropper from moving in or out relative to the surface of the eye, thus the eye dropper can still impact with the surface of the eye. Further, Wood does not use eye pads or any part to prevent an eye dropper from pivoting in an up and down axis of motion across the height of the eye. Thus, Wood only dampens motion in the back and forth across the width of the eye axis of motion.

Campagna (U.S. Pat. No. 3,934,590) exists in the art as a device that attempts to stabilize an eye drop dispenser through use of a tripod with a pillar that rests on the forehead and another pillar that rests on the cheek. However, it does not provide a precise locator. For such a device to be used on both eyes, the device must be used on one eye and then rotated or flipped for use on the contralateral eye, such that the pillar which originally rested on the forehead over the first eye, upon flipping now rests on the cheek below the contralateral eye, and likewise the pillars that originally rested on the cheek below the first eye upon flipping now rests on the forehead above the contralateral eye. Thus, for the device to be flipped and align properly, the user's forehead and cheek must be of the same distance from the bottle since the pillars are not adjustable. Equally symmetric forehead and cheek dimensions are not typical or prevalent among humans, thus the device is not precise and cannot be flipped for a large portion of the population. Furthermore, the pillars are narrow, relatively pointed shafts and with fixed dimensions. Many users may be reluctant to place two pointed shafts near their eyes for fear of sustaining eye injury. Fear is a major barrier to acceptance and compliance. Because the non-adjustable pillars are of fixed dimension and angle of projection, two pillars may not rest on stable bone but instead on the eyelids. Further still, the device only applies drops to one eye at a time and does not allow the administration of drops to both eyes without reposition and realignment of the device. The Campagna design requires three disparate surfaces for device stabilization—nose, forehead and cheek. In contrast, the subject embodiments have three-point fixation, but only require two surfaces for stabilization—nose and forehead.

There exists a need in the art for an eye dropper holder that first locates precisely and also supports, stabilizes, and holds stationary, an eye dropper in all three of the up-down, side-to-side, and in-out axis, and which may function to accommodate both eyes with a single alignment placement by a user. There is a need for a device that can deliver an eye drop without causing reflexive blinking.

BRIEF DESCRIPTION OF THE DRAWINGS

FIG. 4 is a view featuring the bottom of the delivery platform of the device.

FIG. 5 is an edge on top view featuring the pillar supports of the device.

FIG. 6 is an edge on side view featuring the layout of the device.

DETAILED DESCRIPTION

The present application overcomes limitations in the prior art by presenting a new and novel way to enable a person to align and stabilize an eye dropper while applying eye drops to their own eyes in a softer and easier manner. The present application is self locating on the user's face and prevents motion in three directional axes, namely, up and down the face, back and forth across the face and in and out toward the face. The present application also provides two holes for simultaneous eye drop application to both eyes or one eye at a time without moving the platform. The present application also contains a guard to shield the eye dropper nozzle that prevents the eyelash from striking and contaminating the tip of the eye dropper.

The desirable outcome is to optimize precision location of an eye drop application and to minimize wastage. The device offers the advantage of facilitating non-visual alignment of the eye dropper with the eyes, because the device merely has to be placed on the user's face such that the lower nose based support falls on the nasion, where the face and the upper nose join the lower forehead, and which causes the device to be automatically aligned without necessitating any visual input needed to perform alignment. This is a significant distinction because the eyes into which the drops are being placed are the user's visual input sense. Since it is not feasible to put drops into eyes and see at the same time, the ability to perform alignment of an eye dropper to ensure drop delivery without visual input is a feature of the present application. The present application also optimizes efficacy to obtain maximum therapeutic benefit and focused, precise delivery of artificial tears or medication.

One cannot see the eye drop coming because the eye drop delivery is "off visual axis" so the user does not see the drop coming and therefore avoids reflexive blinking. The eye drop dispenser locating apparatus is designed to deliver over the caruncle—a landmark medial to the visual axis.

The present application is usable on both eyes, either singly or simultaneously without flipping the device and does not require a user to place potentially pointed shafts near the eye. The present application may also facilitate bilateral sequential administration of eye drops.

Figure 1A:
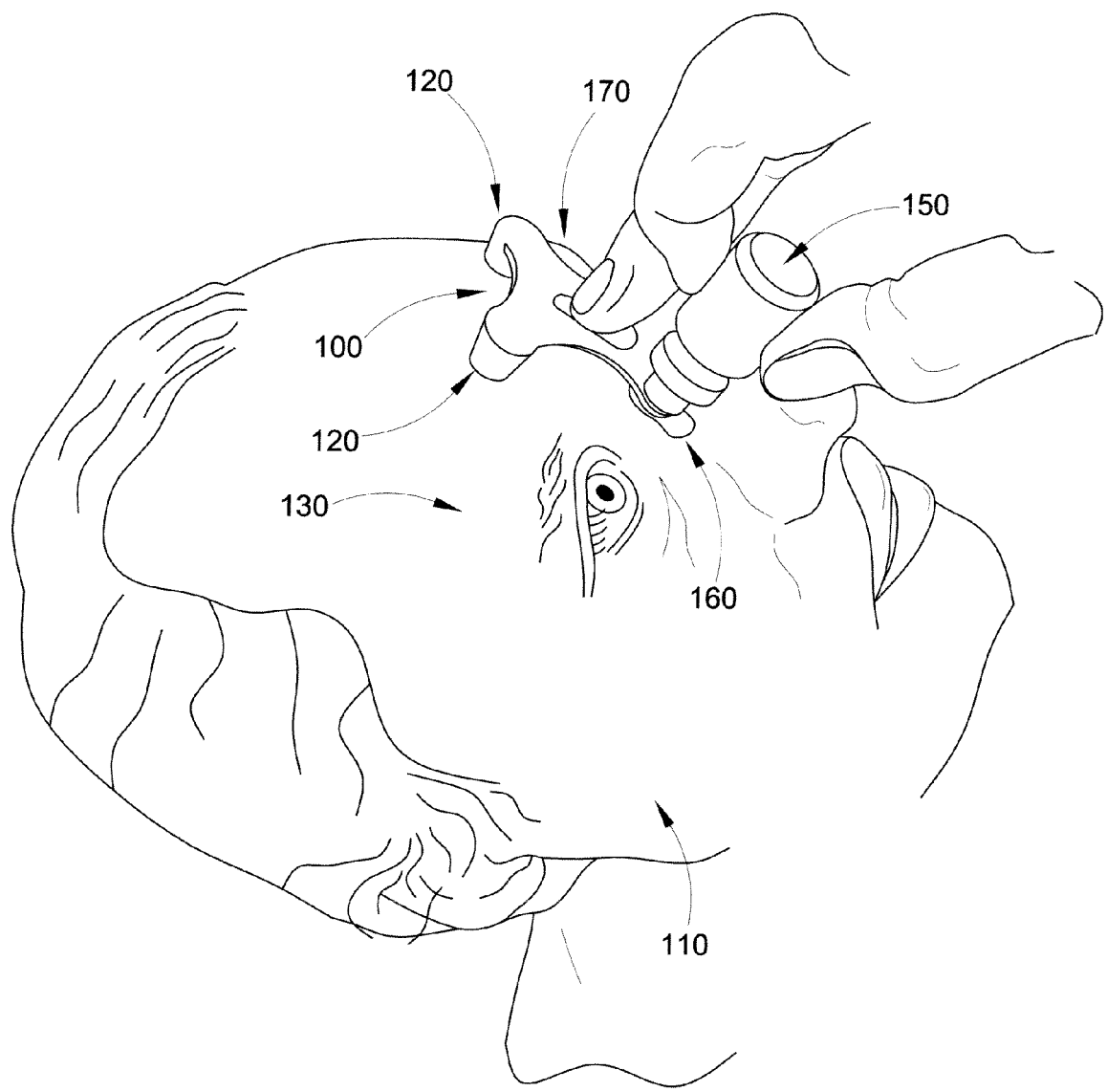
FIG. 1A is a perspective drawing of the device in one-handed use.

Referring now to FIG. 1A, the eye dropper holder is in use with one-hand. The device 100 is placed such that it rests on the user's face 110 by means of a pair of pillars 120 which rest on a user's forehead 130, and a nasal bridge 140 which rests on a point where the upper portion of the nasal bone intersects the lower forehead. The eye dropper 150 is inserted into the available wells 160, 170. A finger is placed in the center of the eye dropper holder in order to apply a pressure necessary in order to keep the device pressed against the user's face 110. Thus, a single hand may align the device relative to the eyes by also being aligned relative to the nasion. In one embodiment, a distance from a bisecting access of the device to the center of a delivery well is the average distance between the center of a human nose and a corner of a human eye. Such a distance from the center of the delivery platform to the center of the delivery well is within the range of from about 0.065 inches to about 1.65 inches.

Figure 1B:
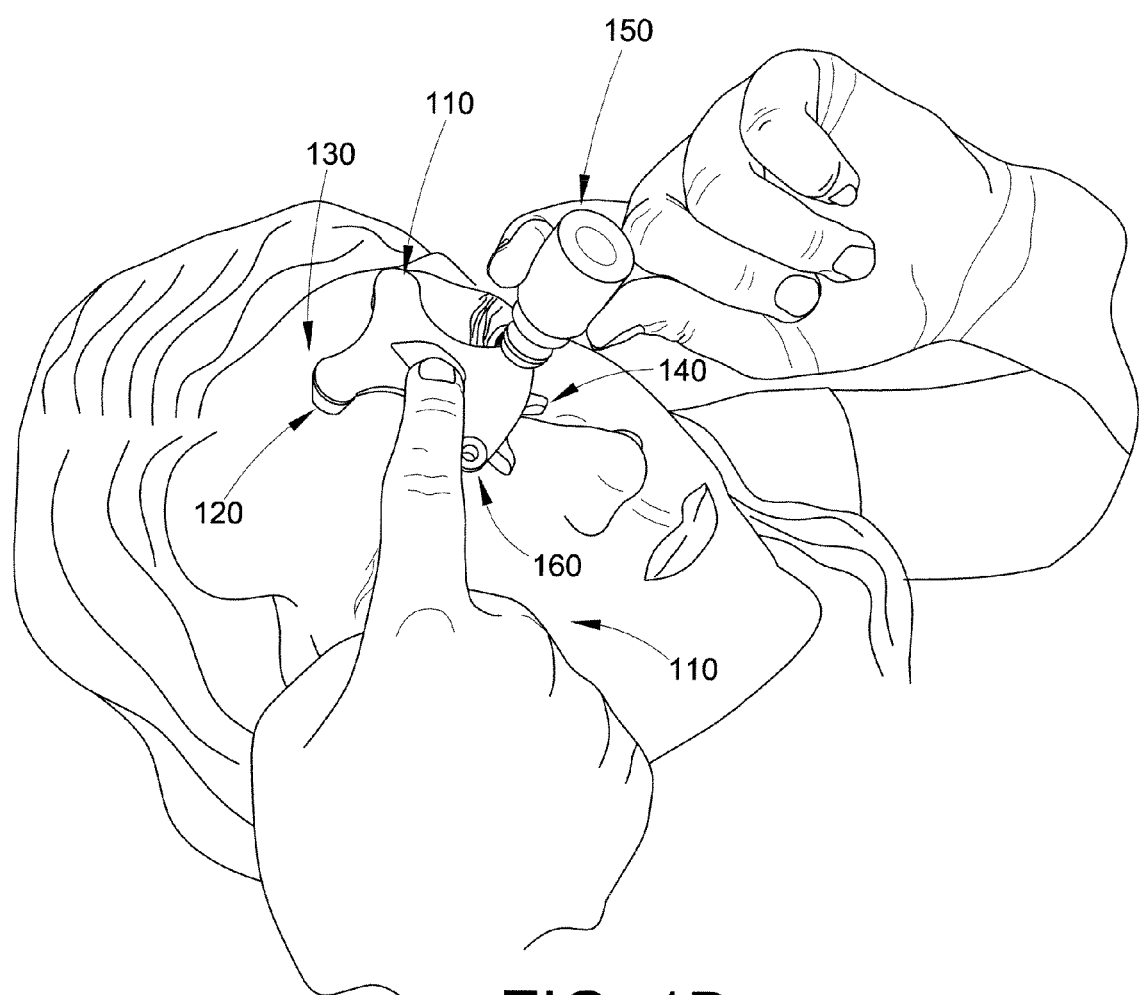
FIG. 1B is a perspective drawing of the device in two-handed use.

FIG. 1B shows use of the device with two-hands. The delivery platform may be held in place against the forehead by a finger of either hand applying suitable pressure to the center of the delivery platform. The opposite hand may then squeeze the eye drop dispenser between two fingers, such as the thumb and forefinger. The head should be tilted backward as the eye drops are applied, an optimal angle being about 60 degrees, from the horizon to an axis running through the user's head. For such an axis, the user standing erect and upright, the axis would be at a zero degree inclination. The axis would be parallel to the level horizon upon which the user stands. By tilting the head backward, the angle between the horizon and the axis would increase until the angle reached about 60 degrees. While tilting the head backward would help facilitate the flow of eye drops, the flow of drops could also be facilitated by squeezing the bottle or by a fluid or water jet.

Figure 2:
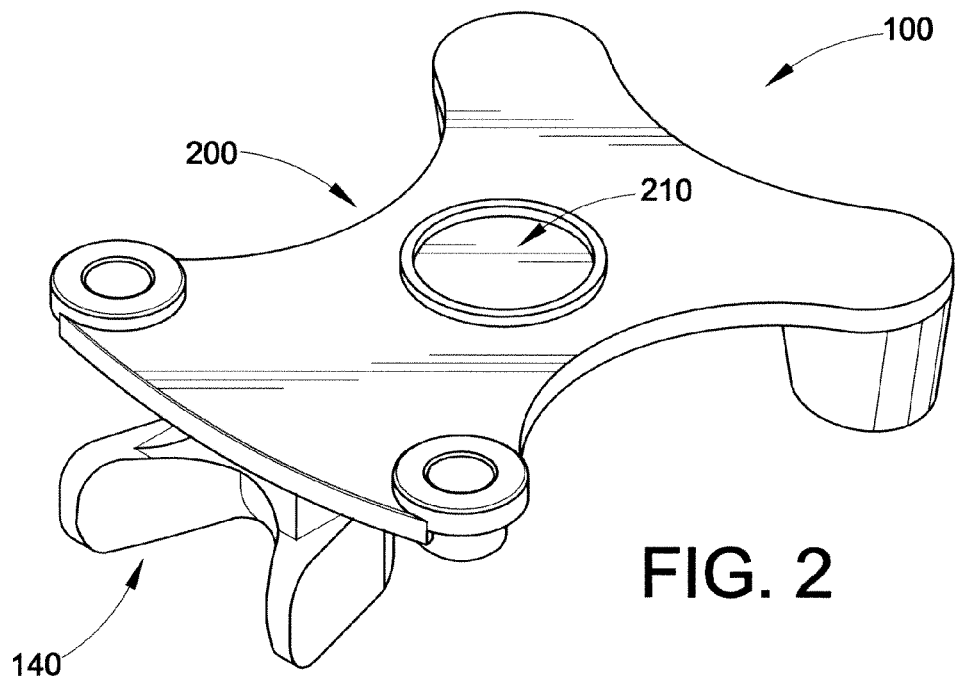
FIG. 2 is a perspective view of the device alone.

Referring now to FIG. 2, the eye dropper holder 100 comprises one fully assembled unit, which may be made up of separately assembled pieces such as, but not limited to, the delivery platform 200, and the nasal bridge saddle or nasal bridge 140, which may be manufactured as one entire part, or the nasal bridge may be manufactured separate from the delivery platform and assembled together and inserted into the delivery platform 200. The eye dropper holder 100 may be made available with the eye drop container already inserted as an attached bottle, without an eye drop bottle attached, or the eye drops may be packaged in a separate bottle with the eye dropper holder device. The eye dropper holder 100 also contains a holding spot 210 at an upper side to which a user's finger may be placed in order to enable the user to hold the eye dropper holder securely in place during use.

Figure 3:
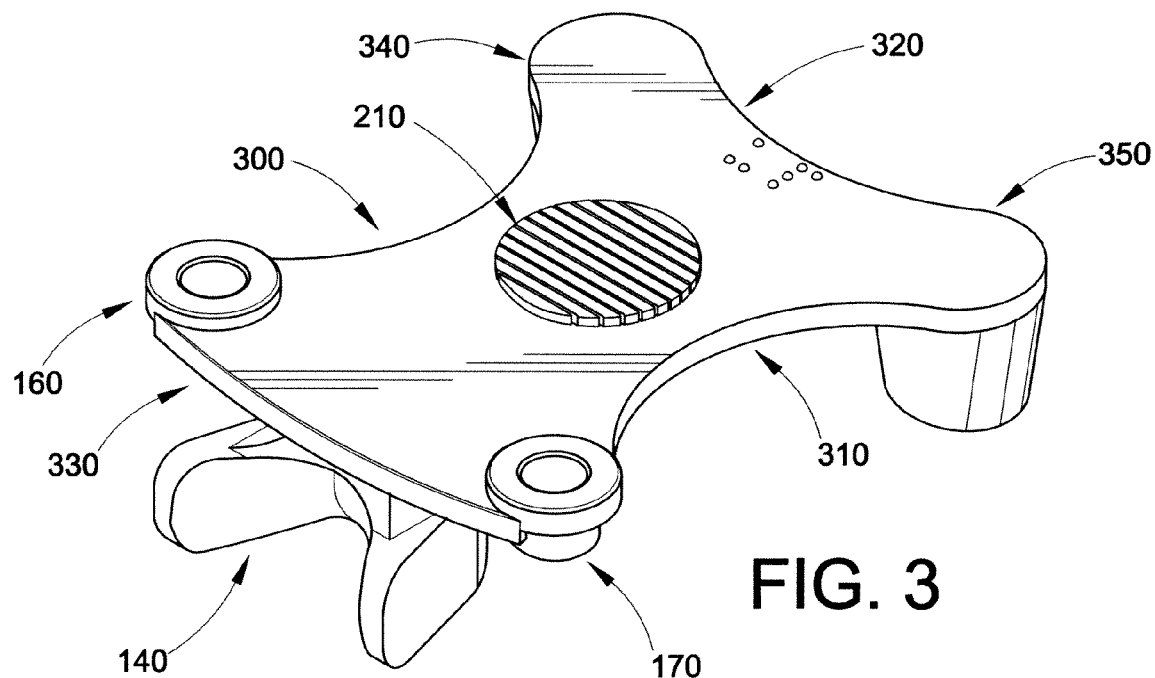
FIG. 3 is a view featuring the top of the delivery platform of the device.

Referring now to FIG. 3, the eye dropper holder 100 is comprised of the delivery platform 200 that is flat and thin. The device could also adequately function if the delivery platform were to be thicker. The delivery platform can be of any geometric shape such as, but not limited to square, rectangle, circle, triangle, and any combination of shapes or polymorphic shape.

The preferred embodiment is a delivery platform 200 which is substantially square, wherein the sides 300, 310 are curved inwardly in an arc shape, with the upper edge 320 being similarly curved with a shallower arc. The lower edge 330 takes the form of an arc that is curving outwardly. The upper edge 320 intersects with the sides 300, 310 for two pronounced semi-circle shaped upper cantilevers 340, 350. The lower edge 330 intersect both the sides 300, 310 by means of smaller semi-circle lower cantilevers, each of which contain a delivery well 160, 170.

The intersection of each side edge 300, 310 with the lower edge 330 produces two pronounced semi-circle shaped cantilevers. These cantilevers each contain a well 160, 170 located such that the center of the semi-circle shaped cantilever and the center of the well are the same point. The wells must pass all the way through the cantilevers in order for the eye dropper to fit and dispense eye drops. A dispensing nozzle of the eye dropper bottle is closely received in the wells 160, 170. Preferably, the wells comprise a nozzle cylinder extending to a vertical limit such that the terminal end of a received bottle nozzle is shielded against any contaminating contact and a dispensed drop may fall through the cylinder without contacting any portion of the inner well of the cylinder. For perspective, the nasal bridge 140 is also shown.

The delivery wells may extend cylindrically in a direction beneath and perpendicular to the delivery platform, toward the user's eye, to form a nozzle cylinder. When an eye drop dispenser is fitted into the delivery well, the tip of the dispenser is contained within the nozzle cylinder. The cylinder prevents the eyelashes from coming in contact with the eye dropper bottle and prevents contamination of the tip of the eye dropper.

A further embodiment of the delivery well is comprised of an inner cylinder and an outer cylinder in order to prevent contamination of the eye drop dispenser. The inner cylinder is tapered, with the upper portion of the well opening on the upper surface of the delivery platform. This opening possesses the largest diameter of the delivery well. The inner cylinder then tapers and becomes narrower as the depth of the well relative to the upper surface of the delivery platform increases. The inner cylinder receives the tip of an eye drop delivery apparatus, surrounding and encompassing the tip of the eye drop delivery apparatus. The outer cylinder is not tapered and exists outside of the inner cylinder, enclosing the inner cylinder. The outer cylinder serves to prevent the eyelash from touching the tip of the eye drop dispenser. An eyelash of a closing or winking eye will strike the outer cylinder instead of striking the tip of the eye drop dispenser because the inner cylinder guards the eye drop dispenser tip. This serves to prevent contamination of the tip of the eye drop dispenser because the contaminant from the eyelash will fall on and be deposited on the outer cylinder instead of falling on the tip of the eye drop dispenser.

The nozzle cylinder accommodates the top or tip of an eye drop dispenser by one of; screw threads in the nozzle cylinder that accommodate the screw thread of an eye dropper bottle, a Morse taper or any other tapered nozzle cylinder that facilitates a frictional fit of an eye dropper bottle tap, or a sliding locking mechanism. Rigidly fixing the eye drop dispenser in place facilitates one-handed application of eye drops by the user.

The delivery platform may also possess a holding spot 210 on the side opposite to the side from which the previously mentioned pillars extend. The holding spot may be a raised portion, a rough portion, an indentation, a protrusion, on any other means which would facilitate placement of a user's finger in order for the user to apply pressure to keep the eye dropper holder in place upon the user's forehead. When the holding spot is an indentation, the indentation may pass all the way through the thickness of the delivery platform, or only partially recessed into the delivery platform. The indentation may be centered in the middle of the delivery platform, or anywhere between an axis running between the two wells and through to the two pillars. The indentation may also be of a particular shape such as, but not limited to a tear drop, a star, a number, letter or other graphical element. The indentation serves the purpose to facilitate a finger such that a user may apply pressure at this specific point to distribute pressure evenly in order to hold the device firmly to the user's face. The indentation may also contain raised letters, engraving, Braille, or a diagram to convey information to the user.

Referring now to FIG. 4, the bottom of the eye dropper holder 100 is comprised of a delivery platform 200 that is flat and thin. When the spot holder is an indentation 400, the indentation may poke outwardly from the bottom of the device. The nasal bridge 140 protrudes from the bottom of the delivery platform 200 and is meant to show the scale relative to the delivery platform.

Referring now to FIG. 5, a view from above 500 shows the pillars or forehead pillars 120 protruding from the upper cantilever 320, wherein each forehead pillar 120, is of any form proportional to support the device for a user, but are shown as substantially circular and hollow 505, 515. The pillars may be solid or partially hollow such that the pillars contain channels. A deluxe embodiment may have a pad within the hollow pillar. The bottom of the pillars 510, 520, may be angled, with the lowest ends 530, 540 pointed toward the inside of the delivery platform and the edges of the pillars 535, 545 facing outward being the longer ends. The two pillars 120 which rest on the user's forehead are short, thick, and placed on the forehead at a height substantially above eye level so as not to provide a threat to eye gouging. The nasal bridge is also shown 140 to scale. The nesting bottle could also attach to the body utilizing a hollow cavity.

Referring now to FIG. 6, the perspective of the length of one pillar 120 and the proportionality of the nasal bridge 140 and the nasal pads 600 are presented. The lengths of the forehead pillar 120 and nasal pad 600 are in proportion to the typical dimensions of an average human being's face. The forehead pillars 120 protrude perpendicular from the delivery platform and also in parallel to the delivery wells 160, 170 within the lower portion of the delivery platform. The underside of the bulge produced by the indentation 400 is also presented.

Figure 7:
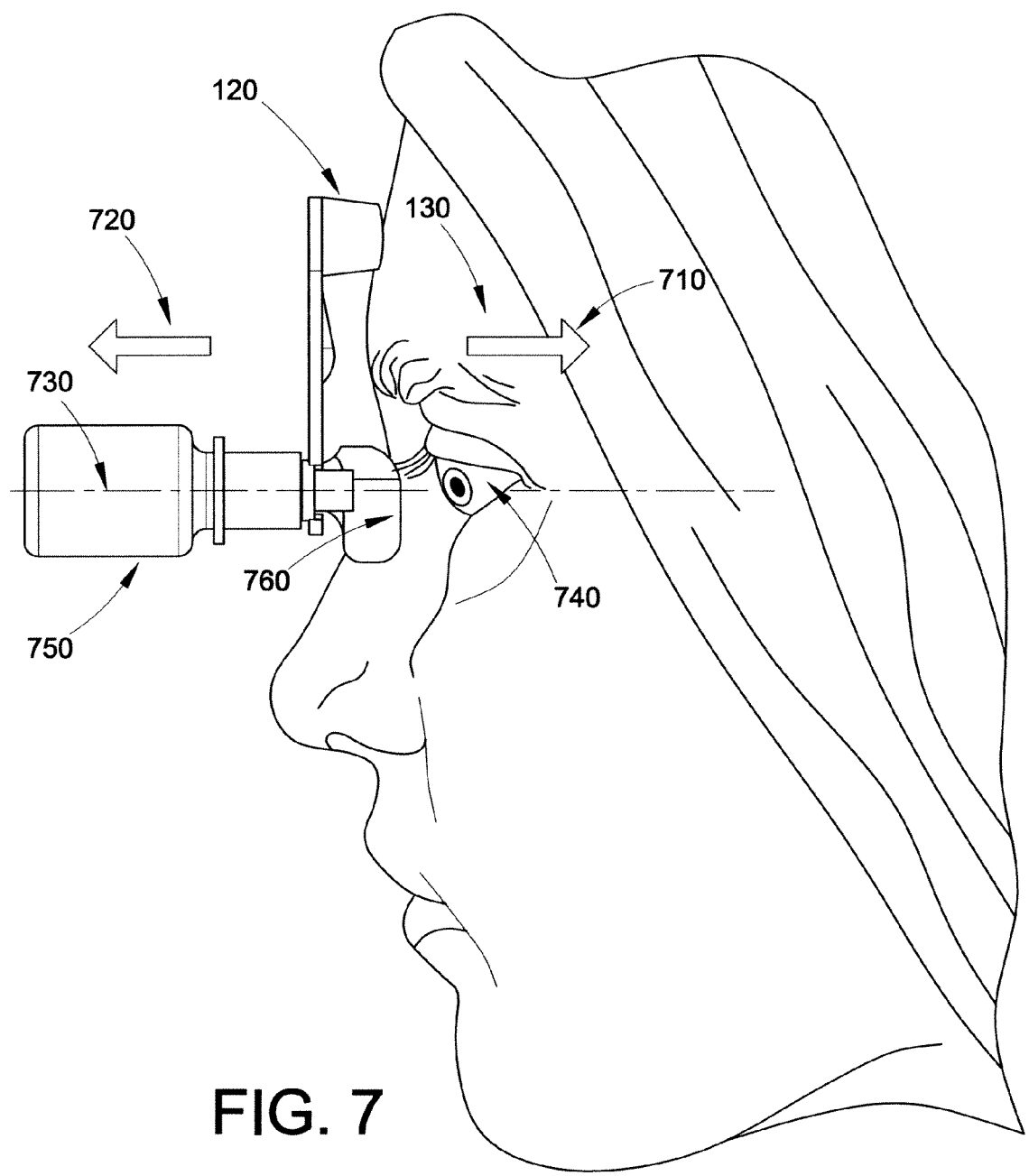
FIG. 7 is a view of the motion dampening in the in and out axis.

Referring now to FIG. 7, the forehead pillars dampen in and out motion. The forehead pillars 120 as applied to the forehead 130, serve to stabilize the device by dampening motion of the eye dropper coming toward the eye 710, or going away from the eye 720 in an in or out, near or far, towards or away from the eye axis 730 with respect to the surface of the eye 740. This prevents the eye drop dispenser 750 from engaging in contact with the surface of the eye 740 or eyelashes to avoid contamination of the dispenser. The eye drop dispenser 750 can be held in place at a distance 760 suspended above the surface of the eye. The distance is relatively closer than prior art holders to minimize drop velocity at contact but is far enough to prevent infections or scratching that may occur when a contaminated eye drop dispenser comes in contact with the surface of the eye. This height precision locking mechanism is useful to prevent eye dropper impact with the surface of the eyeball.

Figure 8:
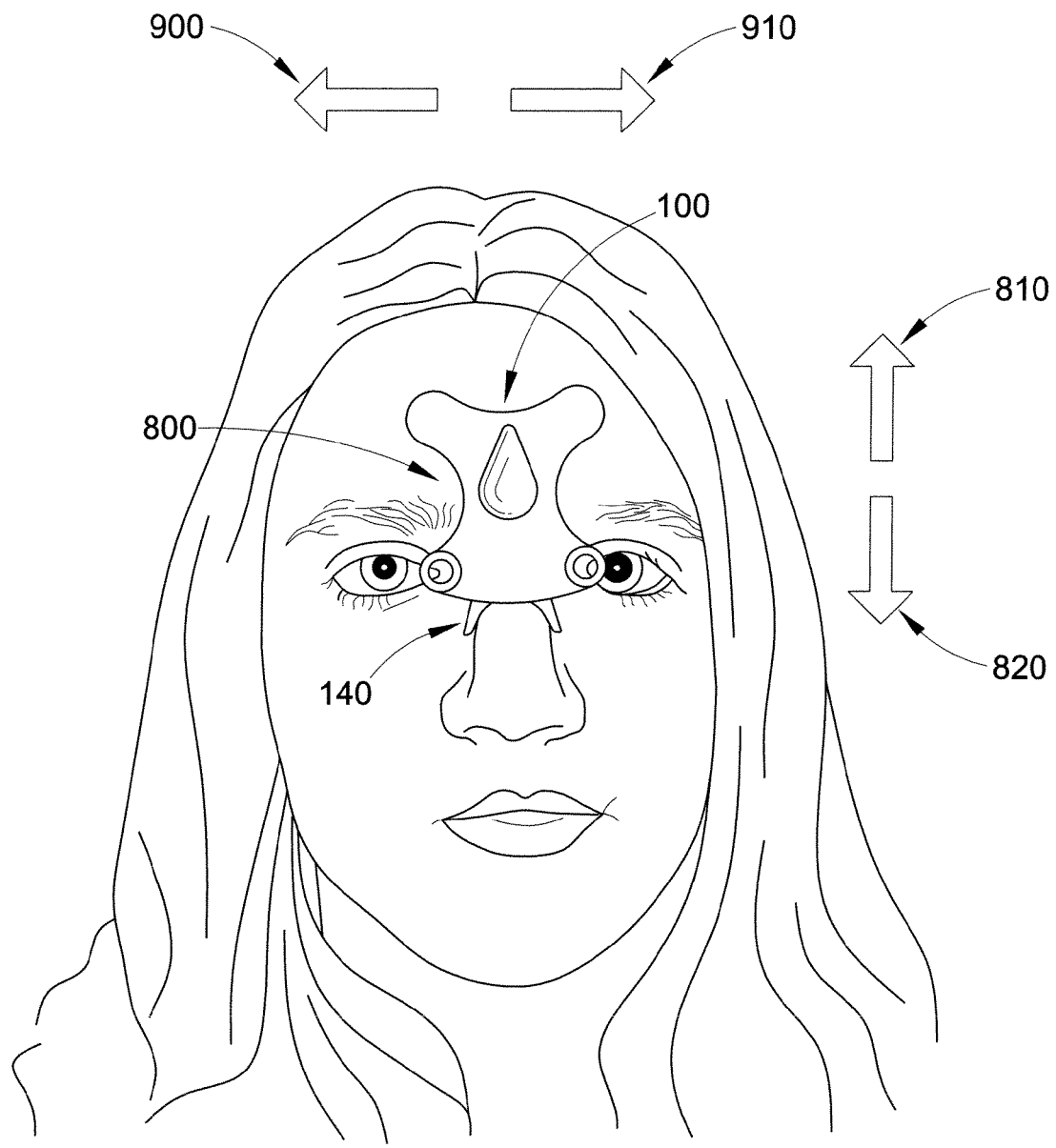
FIG. 8 is a view of the motion dampening in an up and down axis and a side-to-side axis.

Referring now to FIG. 8, the lower portion that dampens up and down motion is presented. The eye dropper holder 100 is seated on the nasal bridge 140 that rests on the nasion or bridge of the nose 800 at the intersection of the user's upper nose and the user's forehead. The small bridge then tapers down into two cantilever supported slightly diverging nose pads, wherein each nose pad occupies a different side of the user's nose as the bridge rests on the user's nasion. Seating of the bridge of the device upon the user's nasion serves to stabilize the device by dampening motion over the face, from forehead 810 to the chin 820 about the up and down axis such that the eye dropper is held in place over a portion of the eye, such as but not limited to, the iris and is prevented from moving to above or below iris. This stability locking mechanism insures that the drops are applied over the proper location of the eyeball.

The nasal bridge 140 sitting on the nose with pads on the side also dampens side-to-side motion away from the nose 900, and toward the nose 910. The bridge pads serve to stabilize the device by dampening motion in a lateral, side-to-side across the face, from ear-to-ear axis of motion because a nasal pad located on the left side of the nose prevents the eyedropper holder 100 from moving to the left, and the nasal pad on the right side of the nose prevents the eye dropper holder from moving to the right. The pads may be somewhat flexible to accommodate different user nose widths at the nasion. Thus, the eye dropper is held in place over a portion of the eye, such as but not limited to the iris, and is prevented from moving to the side of the iris. This stability locking mechanism insures that the drops are applied over the proper section of the eyeball.

Figure 9:
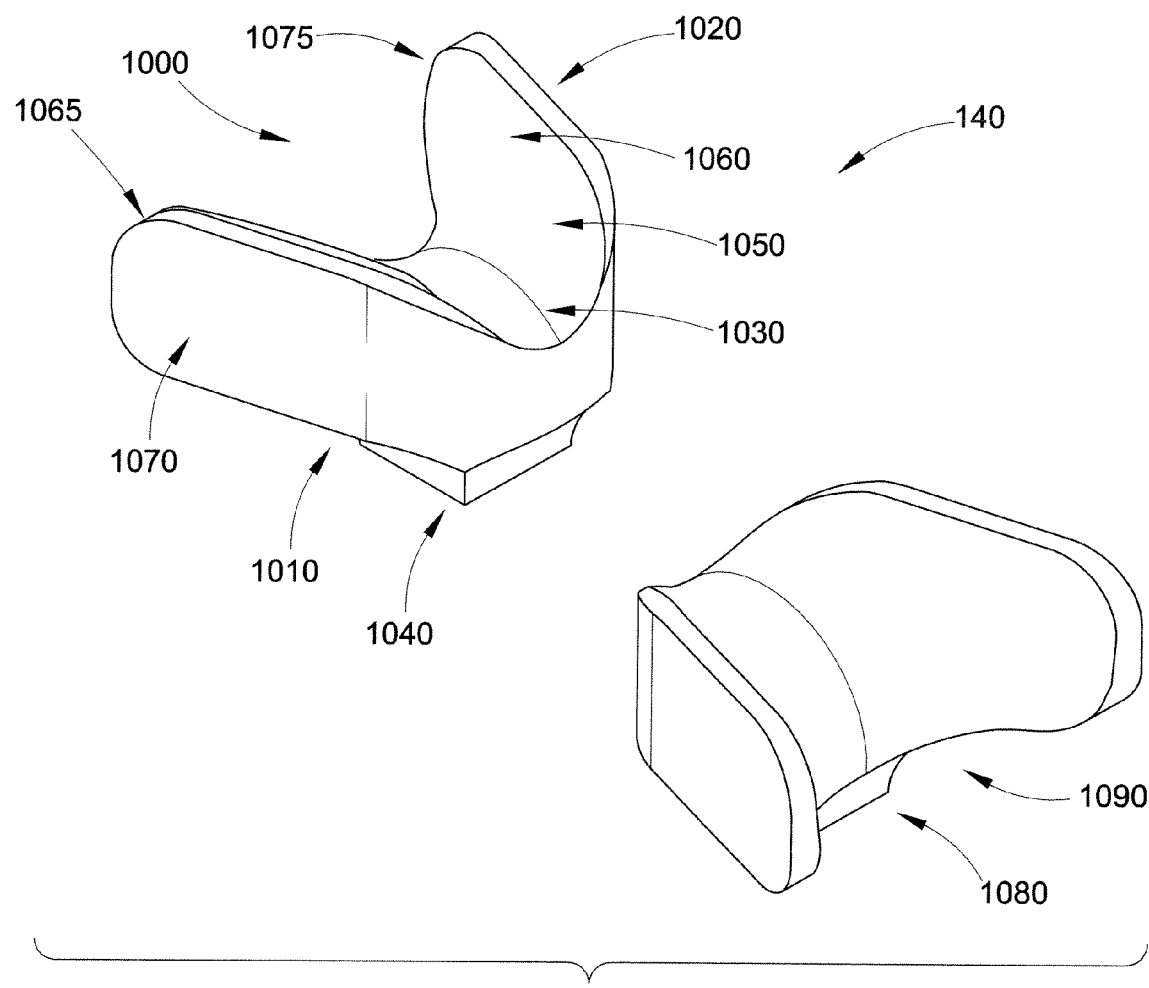
FIG. 9 is a close up detailed view of the nasal bridge saddle.

Referring now to FIG. 9, a close up of the contours of the preferred embodiment of the nasal bridge 140 is presented. As observed from below the delivery platform, the nasal bridge 140 is convex shaped and resembles the shape and form of a saddle with intersecting contours, called a first contour and a second contour. The first contour is substantially thinner and flatter than the second contour. The nasal bridge 140 is symmetric about an axis 1000 that divides a left side 1010 of the saddle-shaped sides from the other right side 1020 of the saddle shape. The center contour of the nasal bridge 1030 is smooth and is disposed through a plane substantially parallel to the delivery platform 1040. The center contour gradually slopes upward 1050 in a direction away from the center axis of the delivery platform 1000, gradually ending at a side 1060 which is perpendicular to the center of the nasal bridge 1030 and perpendicular to the delivery platform at the symmetric axis. This surface 1030, 1050 forms a first contour for mating engagement with a first corresponding contour on the face of the user in a direction on a line going from eye-to-eye. The first corresponding contour attaches to the thinnest part of the bridge of the user's nose or the nasion which runs across the width of the nose and slopes down the sides of the nose toward the corners of the eyes. The sides 1060, 1070 extend in a direction away from the delivery platform and proceed in a direction substantially parallel to the symmetric axis 1000. The ends of the nasal bridge sides are rounded in a semi-circular shape 1065, 1075 and resemble pads that occur on the nasal contact in eye glasses. Another view of the center of the nasal bridge 1080 slopes pronouncedly in a downward direction 1090 such that the edge is perpendicular to the bottom of the delivery platform 200. The entirety of the nasal bridge resembles a saddle shape, with the middle or the bridge comprising the seat of the saddle and the perpendicular sides resembling the horns of the saddle shape. This downwardly sloping aspect comprises a second contour, which mates against a second corresponding contour of the face which comprises the nasion of the face located lengthwise running down from the user's forehead and along the length of the user's nose.

Thus, the ventral aspect of the saddle has a convex surface that conforms to the concave anterior surface of the user's nasal bridge. The wing flap on each side of the saddle conforms to a flat descending surface of the nasal bridge, proceeding in the direction of the medial canthus of each eye. Once the device is placed over the nasal bridge, the form-fitted coupling feature of this component will limit the device's displacement in any direction. Superior displacement of the device along the second contour is set and limited by the descending slope of the mid-forehead between the brows. Inferior displacement of the device is limited by the ascending slope of the nose. Lateral movements are limited by the sides of the nose. The two forehead pillars 340, 350 resting on the flat forehead surface confer added stabilization to the device and prevent tilting of the platform when a bottle is inserted into the delivery well.

Thus, the embodiments comprise a device designed to sit precisely on one part of the nose to assure centration of the delivery well over the medial canthus. A visually-impaired person, by tactile clues, can place the nasal bridge saddle 140 of the device over the nose and feel confident in squeezing the bottle. Likewise, a sighted person can deliver the drop in a pitch-dark environment using this device.

In other words, the subject saddle design conforms to the unique contours to the nasal bridge—a perfect fit like a saddle over the back of a horse. The design molds to the nose and has four-point stabilization—descending slope of the nose at 12 o'clock, ascending slope of the nose at 6 o'clock, and the descending slopes on both sides of the nose at a 3 and 9 o'clock hour. On a side profile, it rests firmly on the depressed contour of the nose—a point that aligns precisely in a horizontal axis with the medial canthus or caruncle. By resting on the saddle pillar on the depressed contour of the nose, it automatically aligns the delivery well over the caruncle—a desirable landmark for eye drop placement.

As the width of noses vary greatly within the diverse size and shape of all people and thus potential users, the nasal bridge may vary in dimension to compensate for this diversity. The nasal bridge may be flexible, made of a material that opens up and spreads widely to accommodate thin and thick nasion widths. The nasal bridge may also be rigid, and come in a variety of sizes and shapes, with varying widths. These various sizes may be provided separately from the delivery platforms in order to allow the users to select the proper width bridge and then attach the proper width bridge to the flat main member. Alternatively, the delivery platform may come for purchase with a variety of width sized bridges, each size packaged with or attached to an individual delivery platform. Finally, one delivery platform may come with a plurality of different width bridges in order to accommodate a plurality of users for the same device, such as a family.

In an alternative embodiment, the nasal bridge may be featured without the nose pads. The nasal bridge may also be interchangeable to accommodate different sized noses, or the nose guard may be made of a flexible material to accommodate different nose sizes. The nasal bridge may also slide in a vertical adjustment manner. Such adjustments may be made to customize the device to an individual user of extreme or extraordinary dimensions.

Figure 10:
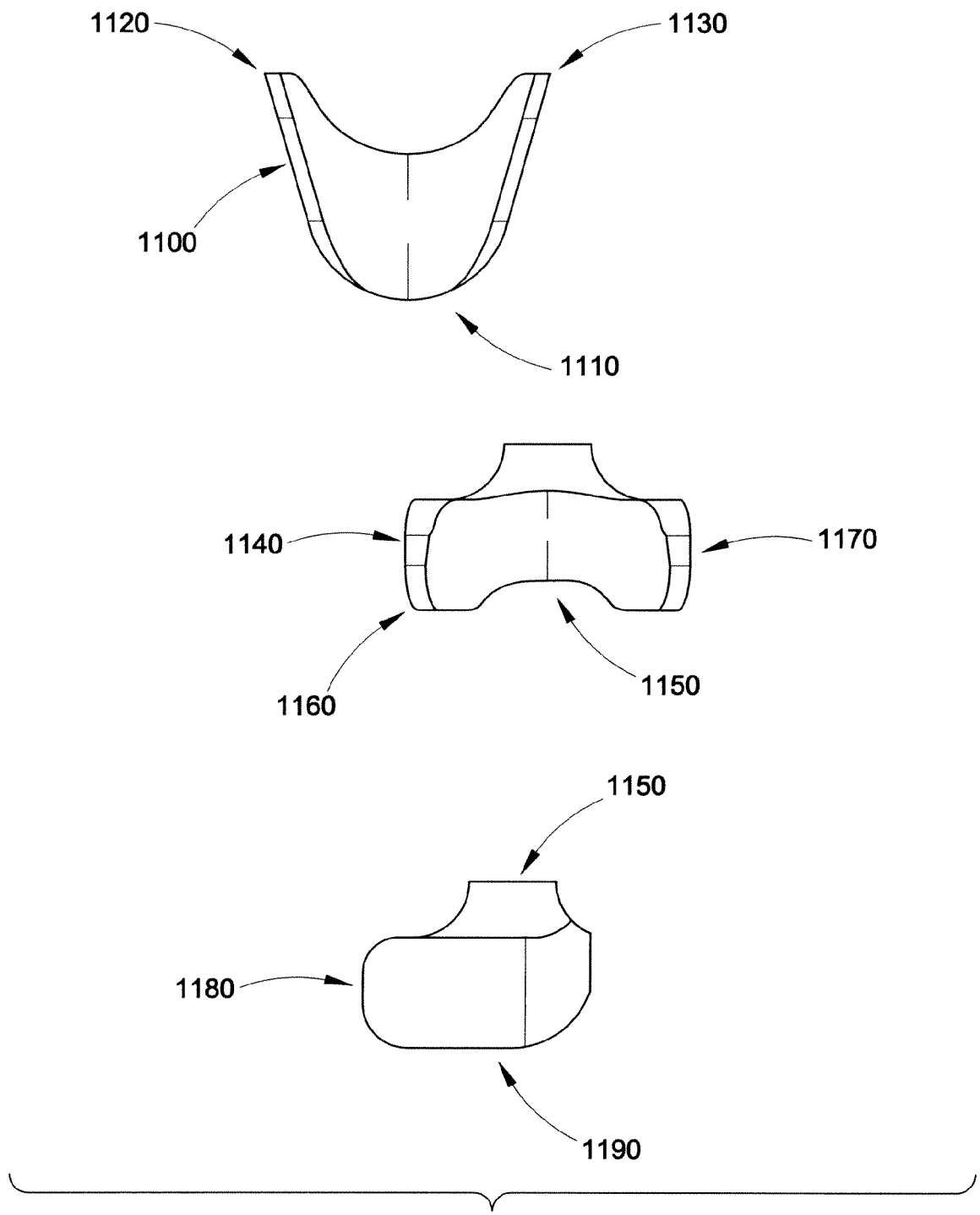
FIG. 10 is a series of views of the nasal bridge.

Referring now to FIG. 10, a series of detailed views of the nasal bridge from above or below, 1100, from the front 1140, and from the side 1180 are presented. The above or below view 1100 resembles a crescent shape wherein the center 1110 of the crescent is substantially thicker than is either one end section or other end section 1120. The center section 1110 gently curves and tapers into the end sections 1120, 1130 which form into the eye pads 1065, 1075. The front view 1140 gradually projects outward from a center point 1150 into two equal and symmetric contours 1160, 1170 which become the eye pads 1065, 1075. The side view 1180 illustrates how the center section 1150 forms into a broad cantilever portion 1190 which eventually forms into an eye pad 1065, 1075.

Figure 11:
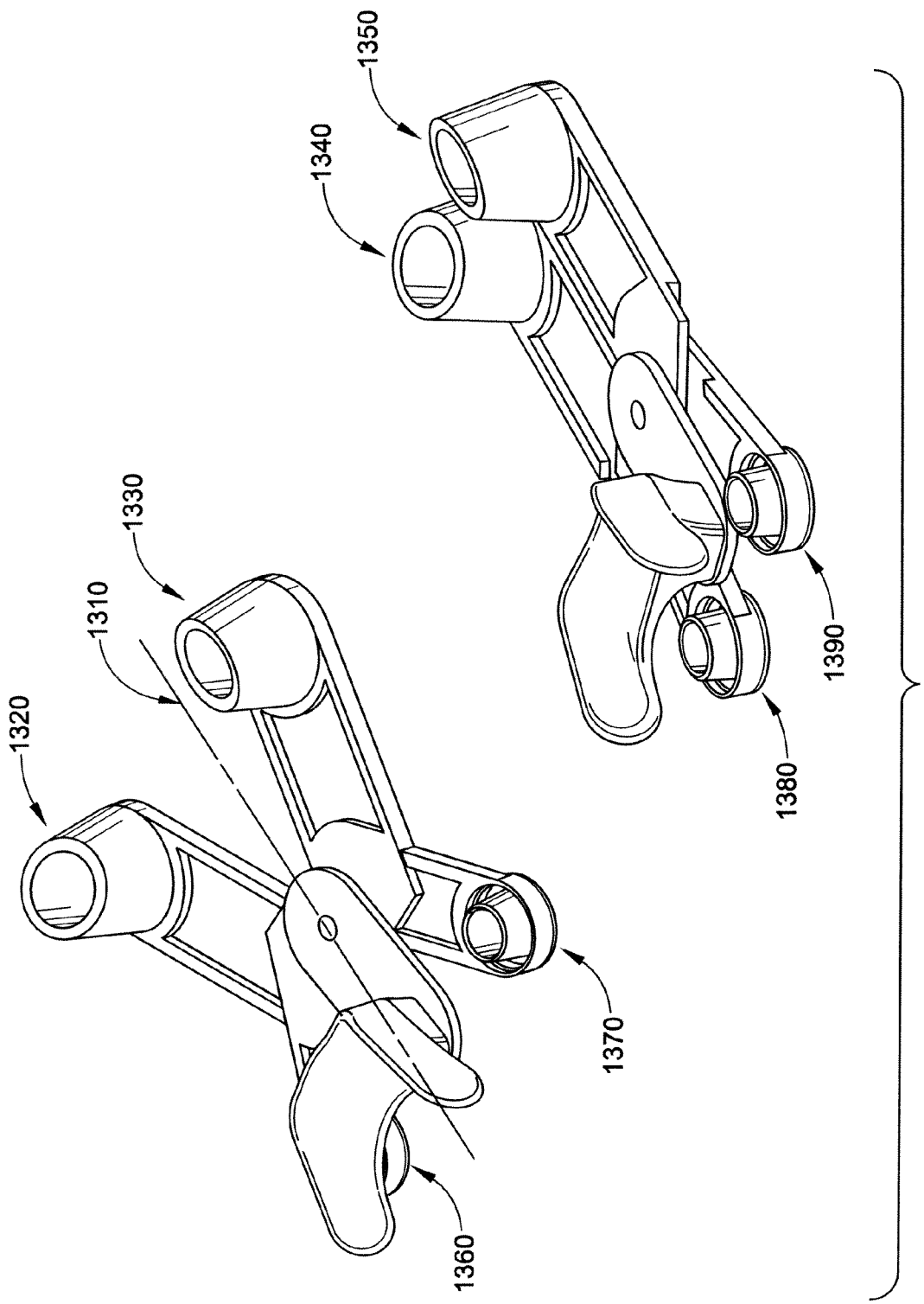
FIG. 11 is an illustration of the collapsible features of the device.

Referring now to FIG. 11, the collapsible features of the eye dropper holder are presented. The eye dropper holder 100 may be folded at least once along the symmetric axis 1310, or at a plurality of other axes. The folding would result in a portion of the eye dropper holder assuming a compressed shape and occupy less space than occupied prior to collapsing.

The upper cantilevers which feature pillars 1320, 1330 are moved into a position closer together 1340, 1350 so as to assume a collapsed form. Similarly, the smaller well containing lower cantilevers 1360, 1370 are also moved into a position closer together 1380, 1390 so as to assume a collapsed form. The collapse of the upper cantilevers may occur in parallel with the lower cantilevers by an internal mechanism or by means of the opposing upper and lower cantilevers 1320, 1370 being connected together on the same manufactured part. The upper cantilevers 1320, 1330 may also move independent of the lower cantilevers 1360, 1370.

Figure 12:
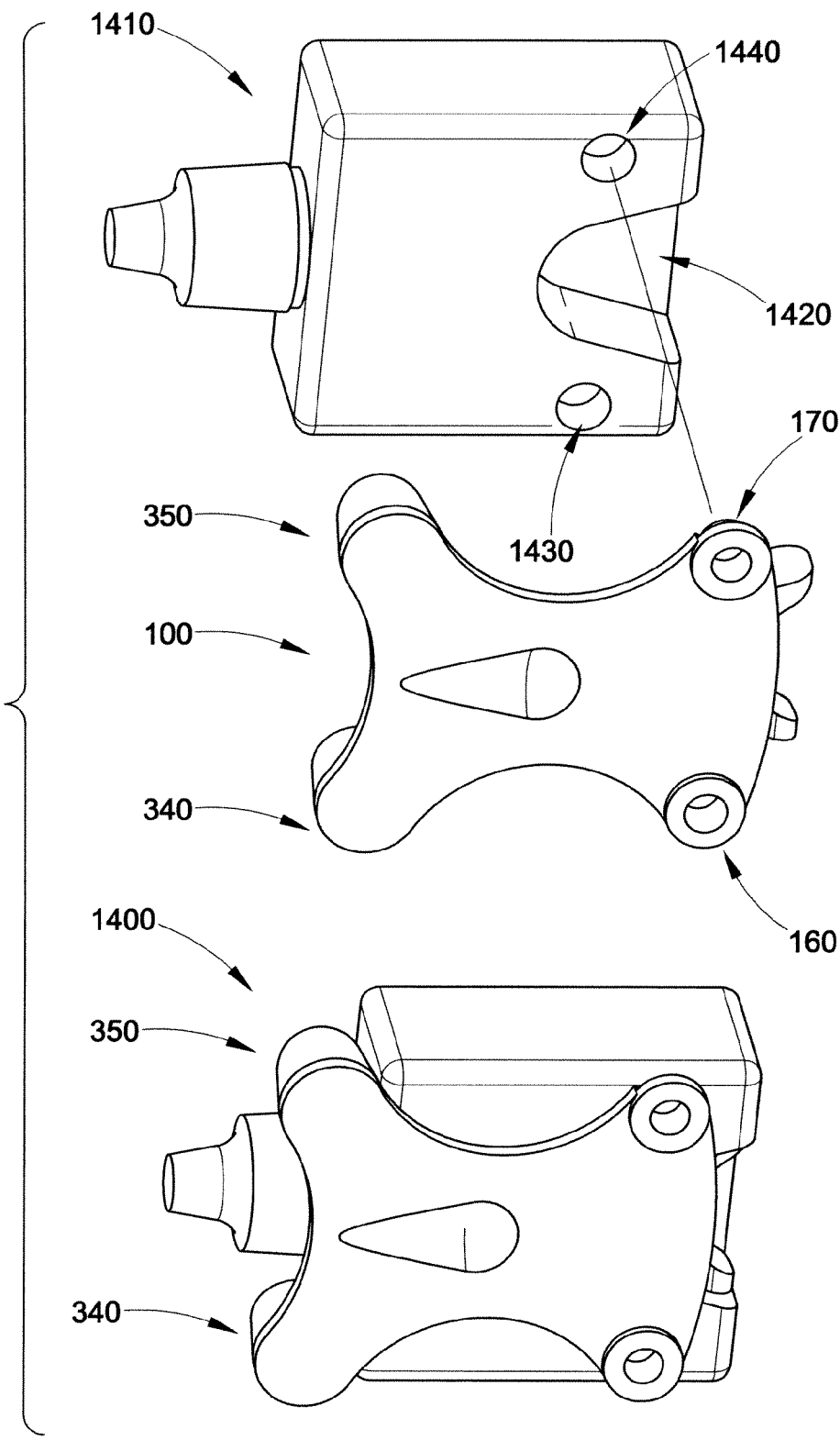
FIG. 12 is an illustration of a possible packaging of the eye dropper holder with an eye dropper.

Referring now to FIG. 12, the packaging of the eye dropper holder with a bottle of eye drops is presented 1400. The bottle of eye drops 1410 is mounted against the eye dropper holder 100 such that the top of the eye drop bottle 1410 is oriented in the same direction as the top of the eye dropper holder 100 and bracketed between the pillars 340, 350 on the eye dropper holder 100. The nasal bridge 140 fits into a slot 1420 on the side and toward the bottom of the bottle of eye drops 1410. The eye drop bottle 1410 also contains two recessed indentations 1430, 1440 which serve to accommodate receiving the lower portions 510, 520 of the cantilever containing wells 160, 170.

Figure 13:
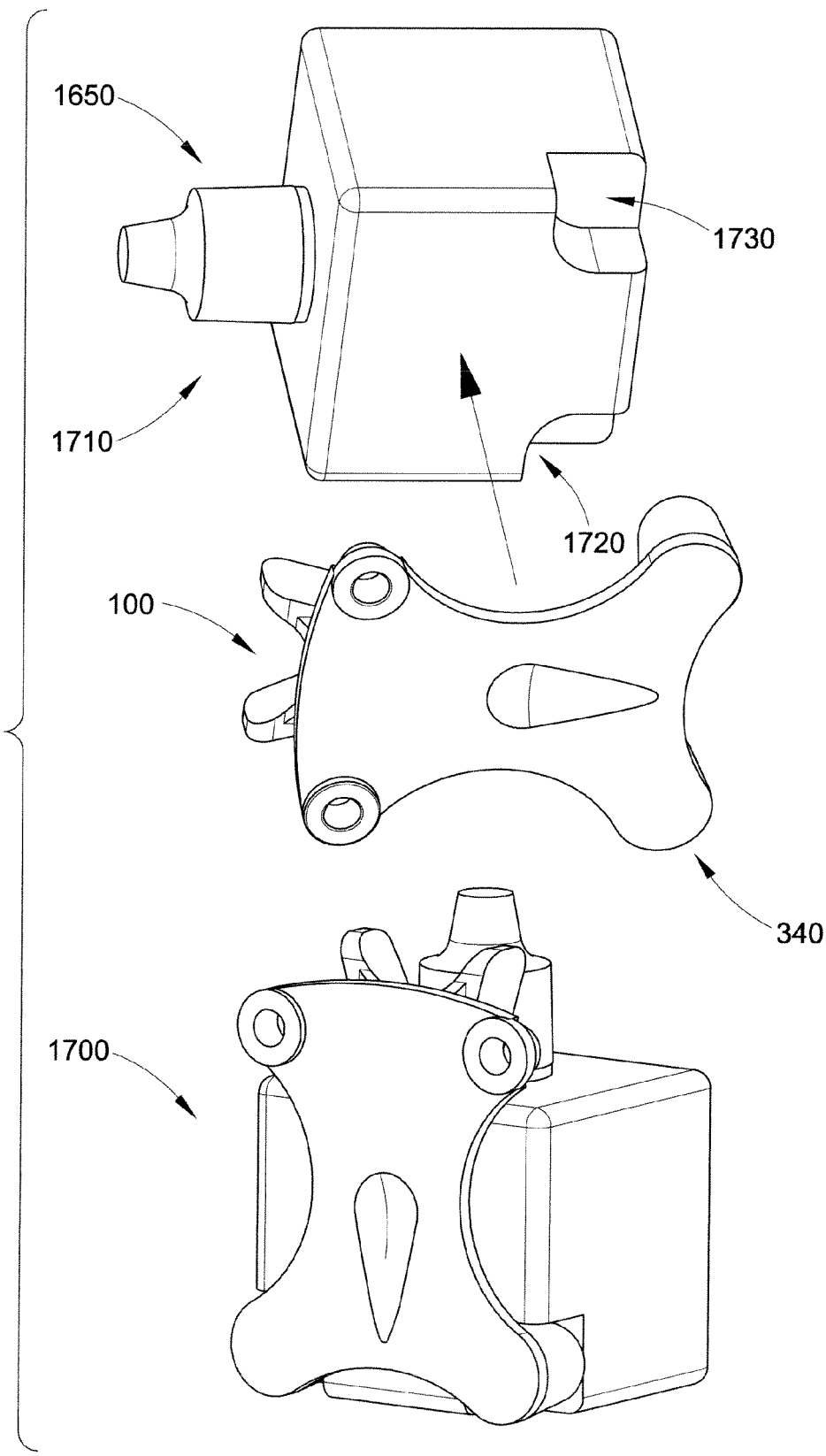
FIG. 13 is an illustration of a different possible packaging of the eye dropper holder with an eye dropper.

Referring now to FIG. 13, a different packaging of the eye dropper holder with a bottle of eye drops is presented 1700. In this packaging, the eye dropper holder is inverted upside down relative to the eye drop bottle and relative to the aforementioned packaging 1400. Here the bottle of eye drops 1710 is mounted against the eye dropper holder 100 such that the top of the eye drop bottle 1650 is oriented in the same direction as the bottom of the eye dropper holder 100 and bracketed between the nasal bridge on the eye dropper holder 100. The cantilevers which support the forehead pillars 340, 350 fit into two recessed indentations 1720, 1730 on the back of the bottle of eye drops 1410.

Figure 14:
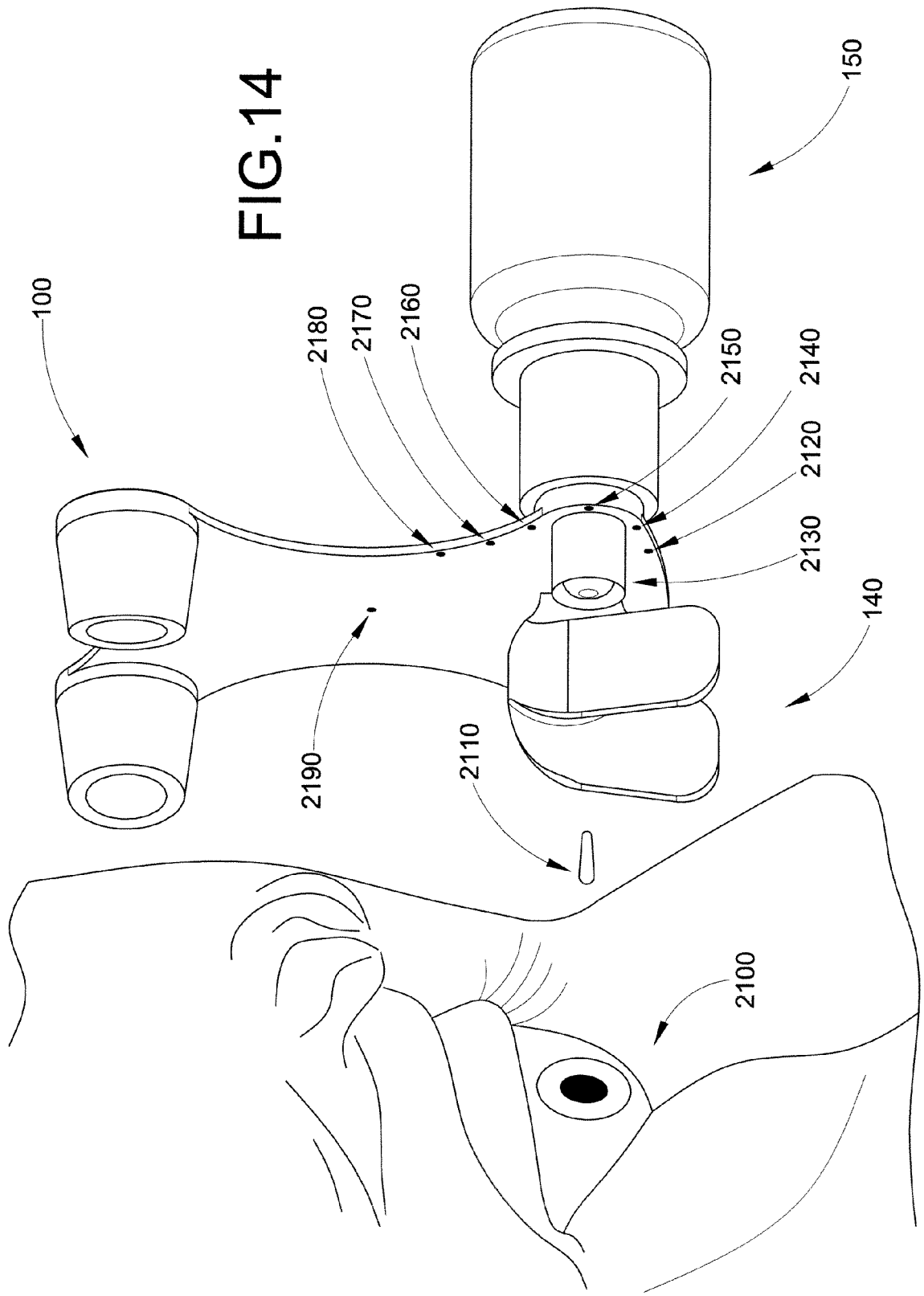
FIG. 14 is an illustration of the various positions of the red dots used for off visual axis alignment.

Referring now to FIG. 14, a system incorporating the eye dropper holder 100 is presented that performs non-visual alignment of an eye drop bottle 150. The system enables eye drops 2110 to be applied to the eye 2100 from an eye drop bottle 150 located in a stable position off of a visual axis perpendicular to the center of a user's eye. Non-visual alignment serves to reduce reflexive blinking associated with the application of eye drops manually. Reflexive blinking is reduced because the user is not looking at the bottle tip for visual alignment. Since alignment can be performed without using vision, the user can stare at a distant target in space. Since the eyes are freed from being used for visual input, a user will not react to the proximity of an eye dropper and thus will not blink reflexively. A user prevented from seeing the eye drop approaching, combined with a lessened sensation of impact upon the eye will not reflexively blink.

More particularly, the relative visual axis is a straight line drawn from the retina through the center of the pupil. An eye dropper dispensing an eye drop from a distance substantially close to the visual axis can be said to be in visual alignment with the visual axis. Whenever the eye dropper is close to or within the visual axis, the user will see the eye drop coming as the drop hits the user's cornea. The user will also feel the drop contact with the surface of the eye. The combination of the two factors responsible for the blink reflex, namely the visual clue and the tactile sensation, will cause the reflexive blinking by the user. The present application is uniquely designed to position the eye drop off of the visual axis and thus lessen reflexive blinking.

The present embodiments contain at least one noticeable, e.g. red, spot 2120 located at a position anywhere on the underside beneath the eye dropper holder such as, but not limited to beneath near the nasal bridge 140, on the lower cantilever 2130, at the edge of the cantilever 2150, in the middle of the lower cantilever 2160, at the intersection of the cantilever near the center of the delivery platform 2170, near the center of an edge of the delivery platform 2170, near the center of the delivery platform 2180, and anywhere on the bottom of the delivery platform 2190. The red spot or red target is in visual axis alignment. The red target on the delivery platform enables the user to focus the eye at the red target directly on visual axis. This prevents the user's focused eye from seeing the tip of the bottle, thus removing the visual clue that the eye drop is approaching the eye until the drop makes contact with the surface of the eye. Thus the eye drops are applied without presenting the user with a visual clue and without a sensation on the cornea, removing a cause of reflexive blinking. An alternative embodiment may also use a hole or a pinhole in the delivery platform to attract the user's eye to look through the hole, in order to focus the eye at a distance.

An explanation of reflexive blinking is presented. Reflexive blinking may also be caused by the speed of the drop hitting the eye. Moving the eye dropper closer to the surface of the eye results in the dispensing of eye drops closer to the surface of the eye, which results in the eye drops having a shorter travel path, traveling a shorter time, i.e., with less time to achieve an impact velocity, and thus having a less forceful impact against the surface of the eye than do other eye drop dispensing devices. It is more desirable to release a drop closer to the surface of the eye to minimize discomfort. The present application enables the eye drop dispenser to be positioned closer to the surface of the eye than do other eye dropper holders. The slower impact speed serves to prevent reflexive blinking and is thus another benefit of using non-visual alignment. Reduction of the tactile sensation of a drop impacting the eye thus precludes the reflexive blinking.

Reflexive blinking may also be caused by the area of the eye where the eye drop impacts. Eye drops aimed at the center of the eye typically strike the cornea, which is the most sensitive part of the eye. A less sensitive part of the eye is the caruncle 2240 at the medial canthus recess, or corner of eye near the nose, and away from the highest point at the center of the cornea. An eye drop administered at a delivery point at a less sensitive part of the eye will also lessen impact and reduce reflexive blinking. The present application features an eye dropper holder that positions the eye dropper at a less sensitive part of the eye at a position over the caruncle. The close proximity of the drop applied by the delivery wells to the nasal bridge permits the placement of the bottle tip closer to the caruncle without touching the eyelashes.

The present embodiments preclude a user from seeing the eye drop coming because the eye drop delivery is "off visual axis" so the user does not see the drop coming and therefore minimizes reflexive blinking.

As noted above, the "visual axis" alignment is when a straight line drawn from that point can align with the retina through the center of the pupil. If the eye can see a red spot or red dot on the bottom of the platform, then the red target is in visual axis alignment. If the user can see the tip of the bottle positioned perpendicular over an eye for delivery, then the tip is in alignment with the user's visual axis. As such, the user will see the drop coming, and when it hits the eye the user will feel the contact. While this delivery system gets the drop to the eye, it will not eliminate the blink reflex because it has not abolished the two factors responsible for blink reflex—visual clues and tactile sensation.

The subject embodiments position the drop point "off visual axis" because the user is looking at a red target ("on visual axis") on the bottom of the platform. Since the user cannot see the tip of the bottle, he/she has no visual clue as when the drop is coming until it makes contact with the eye. And since the drop point is situated over the caruncle and off axis, the eye drop will never strike the sensitive cornea. No visual clue and less sensation are two desirable features to minimize reflexive blink.

Another advantage of the present embodiments is that the drops fall into the eye from a lower point and have lower velocity (closer to the eye without touching). This also prevents reflexive blinking and is another benefit of using non-visual alignment. Incidence of a drop hitting the cornea at higher velocity will increase tactile sensation. Therefore, it is more desirable to release a drop closer to the surface of the eye to maximize comfort. The close proximity of the delivery wells to the nasal bridge permits the placement of the bottle tip closer to the caruncle without touching the eyelashes. Lowering the platform results in less velocity when the drop hits the eye.

The delivery point is to the caruncle at the medial canthus recess (corner of eye near the nose), that is, closer to nose and away from the highest point (center of cornea). Because of this reflexive blinking is minimized.

The device is calibrated, by virtue of the location of the two round wells on the platform, to deliver an eye drop only to the medial canthus recess area—the less sensitive part of the eye. Any design that does not control the precise location of the "drop zone" will land the drop on the cornea—the most sensitive part of the corneal surface.

A slight manipulation of the bottle (tip it ever so slightly) is allowed. One can pivot or pivot the bottle around the neck of the delivery well. This is what is meant by "oblique alignment". The drops will still fall down the center of the wells and avoid contaminating contact with the well inner walls.

Exemplary dimensions are such that the plane of the delivery platform 200 is 1 cm from the nose guard when resting on a flat surface. The bottom of the delivery well is 7 mm from the flat surface which shows that the plane of the delivery platform is well above the cornea. For one with a flatter nasal bridge, the delivery platform can be closer to the eyelashes. However, the lashes do not touch the eye drop holder because the delivery well is closer to the medial canthus. The nozzle cylinder projects 4 mm below the ventral surface of the delivery platform. This cylinder serves as a barrier on protecting the sterile bottle tip from coming into contact with bacteria on the eyelashes.

Figure 15:
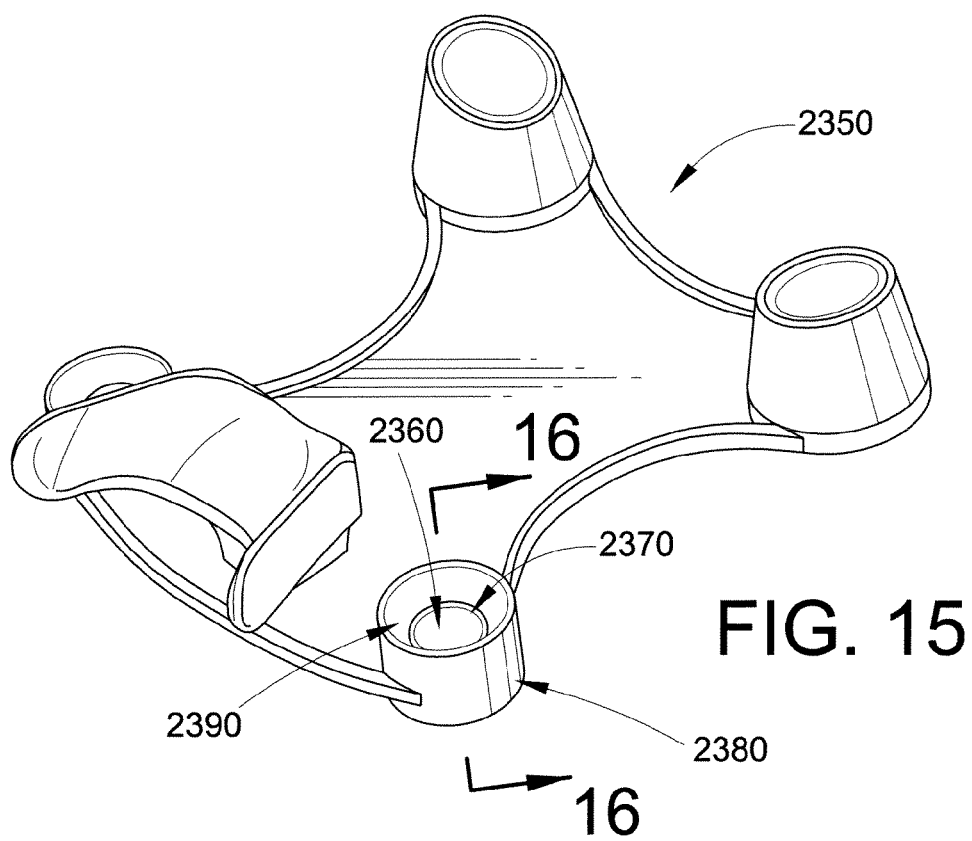
FIG. 15 is an illustration of the tapered delivery well.

Referring now to FIG. 15, the tapered delivery well is presented in greater detail. The top view 2300 of the delivery platform shows the delivery wells 2310, 2320 each comprise an opening leading to a hole. The hole is at its largest diameter at the top of the delivery platform and gradually tapers to become smaller in diameter as the depth of the hole 2330 increases relative to the top side of the delivery platform. The delivery wells may be flush with the delivery platform 200 or in an alternative embodiment, may rise a few millimeters above 2340 the surface of the delivery platform 200. The bottom view 2350 illustrates how the tapered holes 2360 gradually reach the minimum diameter 2370. Also illustrated is a not-tapered outer portion 2380 of the delivery well. This outer portion may be independent of the inner portion. Alternatively, both the inner and outer portions may be connected by a portion 2390 that tapers outward from the bottom of the inner portion of the delivery well to the inner portion of the delivery well. Referring back to FIG. 20, the tapered delivery well 360 is demonstrated in proportion to the rest of the delivery platform 2000.

Figure 16:
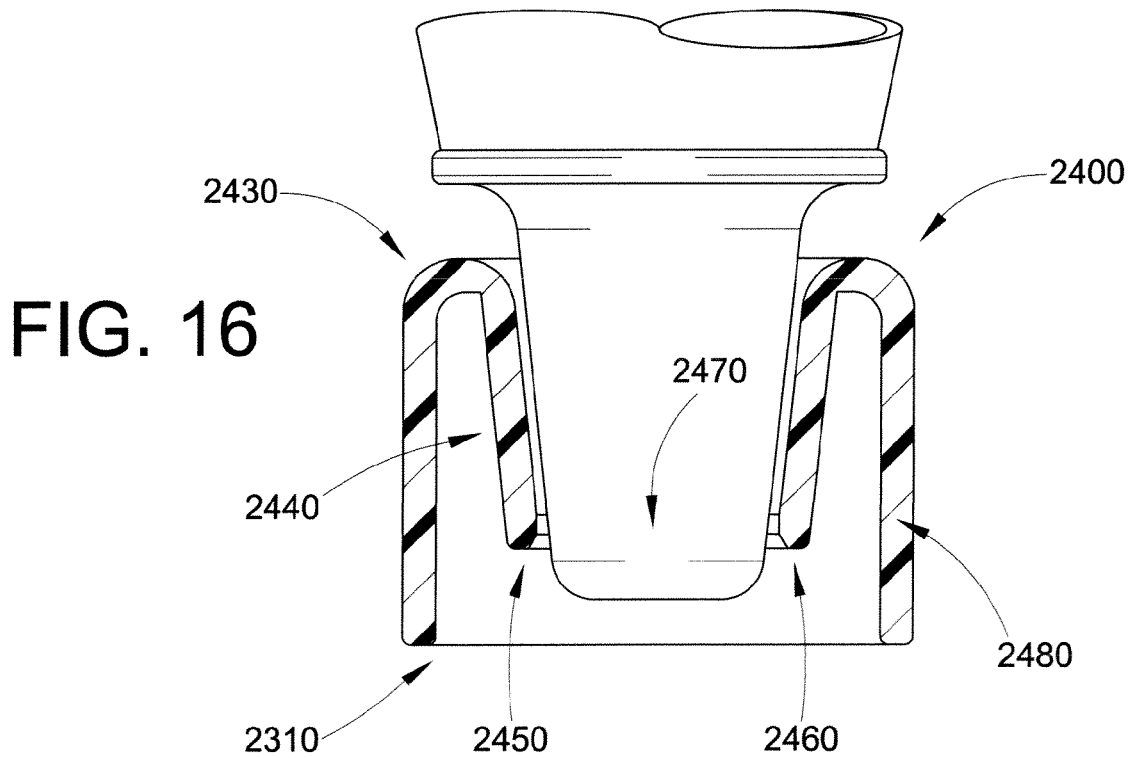
FIG. 16 is a detailed sectioned view of the delivery well.

Referring now to FIG. 16, a detailed sectioned view of the delivery well is presented. The section is drawn across the diameter 2410 of a delivery well 170 and bisects the delivery well in an axis parallel to the axis that bisects the delivery frame 2420 into two symmetric parts. The top of the delivery well is located on the top side of the delivery platform. The top 2430 of the delivery well 2310 gradually tapers with decreasing diameter 2440 and decreasing circumference dimensions as the depth below the surface of the delivery well below the surface of the delivery platform increases. Eventually, a depth of the delivery well is reached where a final and smallest diameter of the delivery well 2450 is achieved where the taper ends. The delivery well may end at this depth, or the delivery well may continue to a greater depth. This outer portion of the delivery well 170 may be independent of the inner portion 2460. Alternatively, both the inner and outer portions may be connected by a portion that tapers outward from the bottom of the inner portion of the delivery well to the inner portion of the delivery well. The eye drop dispenser nozzle 2470 is also tapered and will fit within the tapered delivery well 2400. The match of the delivery well taper with the taper of the eye drop dispenser nozzle makes for a snug fit and holds the eye drop dispenser in place while the drops are applied. Alternatively, the delivery well may be made of a material or a surface texture that increases friction resistance and further facilitates solidifying the contact between the delivery well and the eye drop dispenser. The cross hatching 2480 is not indicative of any specific material, although the preferred embodiment comprises a plastic composition. However, other materials could also be used including but not limited to wood, metals, Styrofoam, paper, and composite resins.

Figure 17:
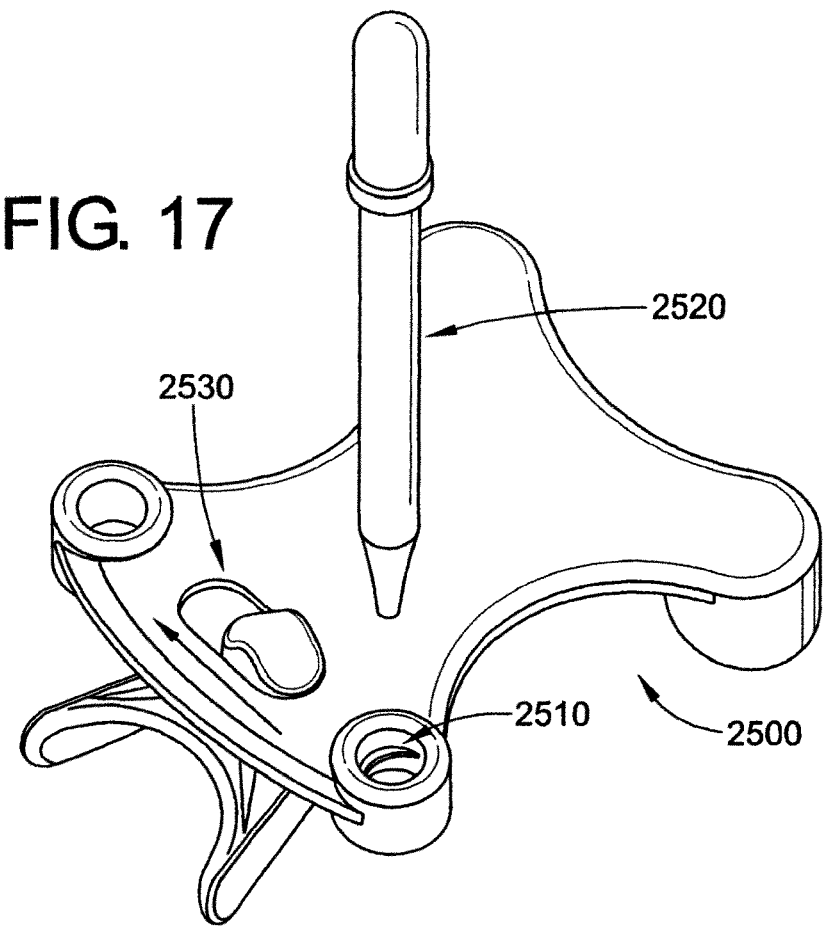
FIG. 17 is a blade for securing eye dropper.

Referring now to FIG. 17, an alternative embodiment of the manner in which an eye dropper may be held is presented. Here, each delivery well 2500 contains a blade 2510 located within the inner surface 2520 of the delivery well such that the blade 2510 is recessed into the side of the delivery well. In order to retain the eye dropper, the blade 2510 extracts from the recess location, enters the space within the delivery well, and presses against the tip of the eye drop dispenser. The blade 2510 presses against the eye dropper on a side and pushes the opposing side of the eye dropper 2520 against the side of the delivery well such that the tip of the eye dropper, and thus the entire eye dropper itself, is held firmly in the delivery well of the delivery platform. The blade 2510 is controlled by a toggle switch 2530 or any other controlling means or apparatus located in the center of the delivery platform. The toggle switch 2530 may control a plurality of blades 2510 on some, any or all of the delivery wells 2500 on the delivery platform. In the pictured embodiment, the toggle switch 2530 may move from one side of the delivery platform to the other side of the delivery platform and tighten the eye dropper by pressing the blade 2510 against the delivery well 2500 closest to the engaged toggle switch 2530 or, in an alternative embodiment, tightening the delivery well furthest from the engaged toggle switch.

Figure 18:
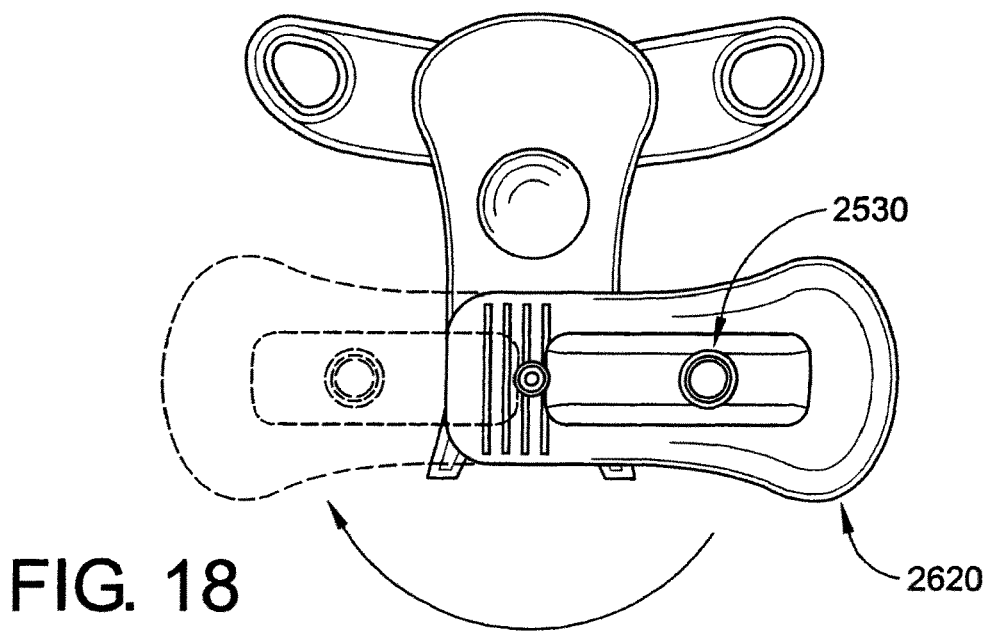
FIG. 18 is a delivery well rotating platform.

Referring now to FIG. 18, an alternative embodiment 2600 of the manner in which the delivery wells are positioned on the delivery platform is presented. In the present embodiment, the delivery platform contains an arm 2620 which swivels or rotates, alternating in position between the left eye and the right eye. Each arm contains a delivery well 2530 for insertion of the eye dropper apparatus.

Figure 19:
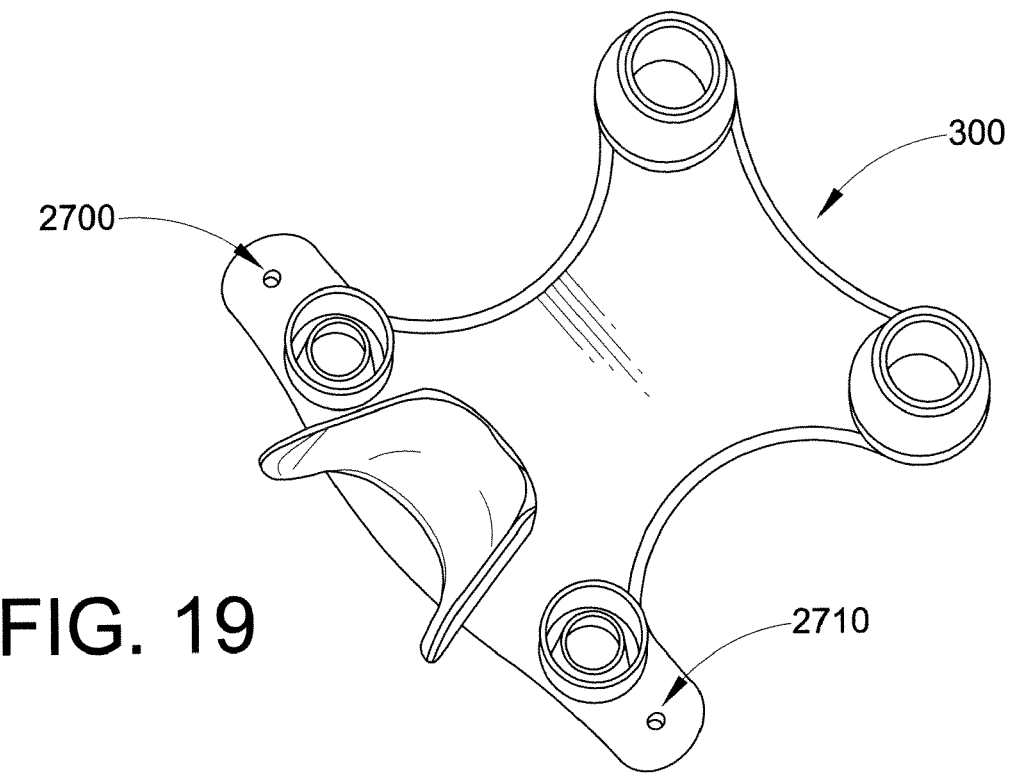
FIG. 19 illustrates a thru-hole focal point.

Referring now to FIG. 19, an alternative embodiment of the manner in which the user's eye may be directed to draw the eye off the visual axis is presented. This embodiment uses thru-hole focal points 2700, 2710 which perform the same function as the red dots 2120, presented previously in FIG. 14. The thru-hole enables the user to focus on a line of sight through the hole and into a distance area.

Figure 20:
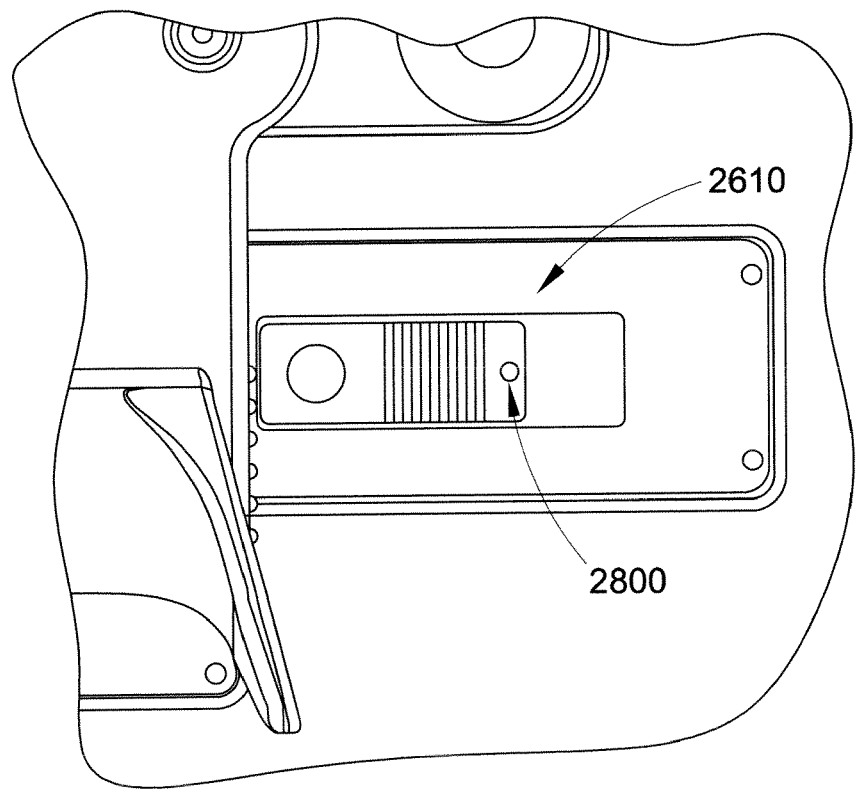
FIG. 20 illustrates a sliding delivery well and thru-hole focal point combination.

Referring now to FIG. 20, this embodiment provides a slider 2610 where both the delivery well and the thru-hole focal point 2800 are located. This enables the delivery well and the thru-hole focal point to be moved simultaneously through performing the same mechanical sliding action. Thus, the distance from the center of the delivery platform to the center of the delivery well can be any distance between the center of a human nose and the outer corner of the human eye.

Figure 21:
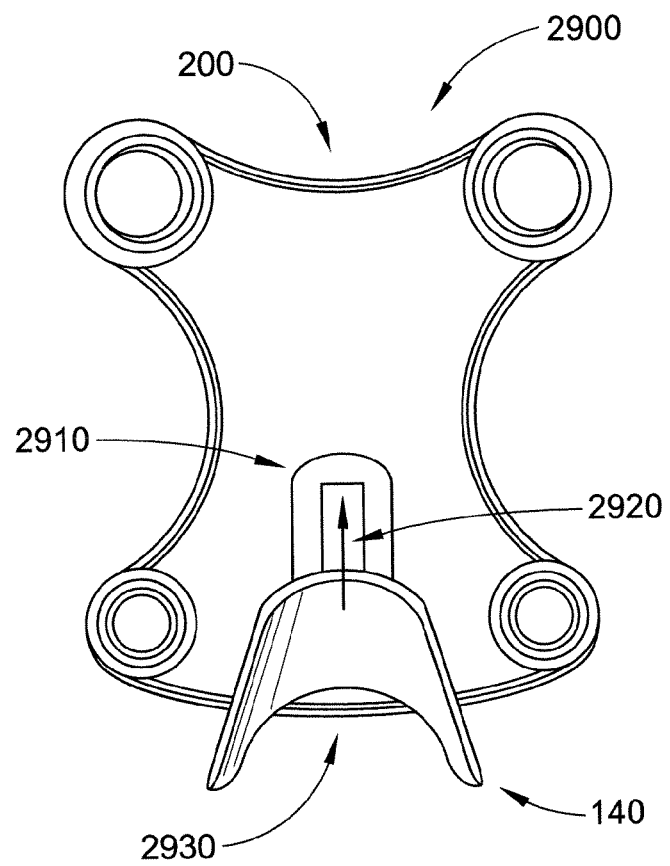
FIG. 21 illustrates a sliding nasal bridge.

Referring now to FIG. 21, an alternative embodiment of the manner in which the nasal bridge 140 is implemented is presented. The nasal bridge 140 may be adjustable in the vertical axis 2920 on the user's face, which runs up and down from the user's forehead to the user's neck. The bridge 140 is substantially similar to the nasal bridge presented previously in the application; however, in the present embodiment, the nasal bridge is attached to a slider 2920 located in a slider track 2910 located on the bottom surface of the delivery platform 200. The nasal bridge 140 can slide anywhere in the slider track 2910 from being located on the bottom 2930 of the slider track 2910, to the middle 2940, to the top 2950 of the slider track 2910. The sliding may be performed by movement of the nasal bridge 140 and tugging the nasal bridge up or down the slider track 2910. Alternatively, the slider may be operated by a lever, button, toggle switch or any other type of control device located on the delivery platform. A focal hole (not shown) such as in FIG. 20 can guide a user to operate the slider in a manner that the delivery well is in a proper position.

Figure 22:
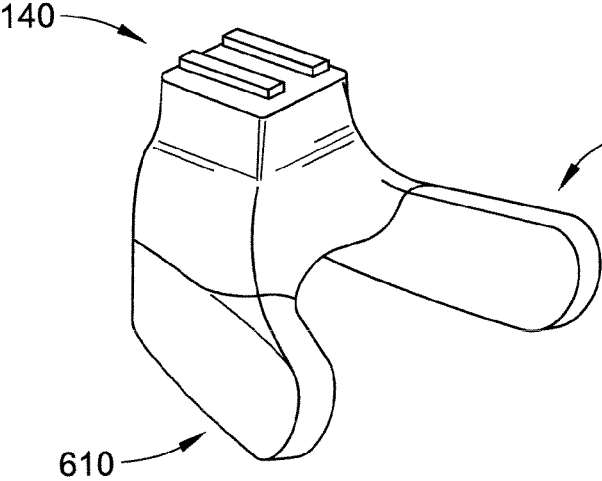
FIG. 22 illustrates a flexible nasal bridge.

Referring now to FIG. 22, a nasal bridge with flexible nasal pads is presented. The nasal pads 600, 610, also known as wings, may be made of a flexible or deformable material that allows the pads to be moved in and out, such that one pad 600 moves closer to or away from the other pad 610. The moving pads 600, 610 accommodate varying sizes of user nose widths. Such a material may be comprised of, but not limited to rubber, elastic, ceramic, putty, metal, foil and the like.

Figure 23:
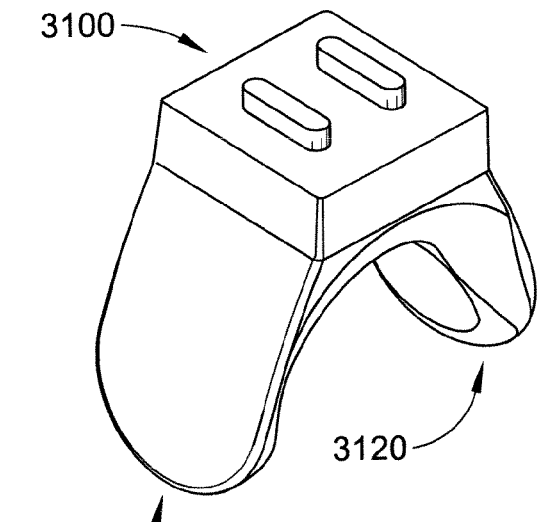
FIG. 23 is a nasal bridge without nose pads.

Referring now to FIG. 23, an alternative embodiment of a nasal bridge 140 without nasal pads 600, also called wings, is presented. Comparing the alternative embodiment with FIG. 10 illustrates how the present alternative embodiment is different. The nasal bridge 3100 presented here, has sloping cantilevers 3110, 3120, but lacks the nasal pads which exist in the previous version 1070, 1075. The top or bottom view 3130 illustrates that the detachable nose bridge 3100 has a pair of cantilevers 3140, 3150 which serve to project downward such that the center of a user's nose placed within the center 3160 of the nasal bridge 3100 would receive a cantilever on either side of the nose. A sectioned view 3135 of this top bottom view is presented. A side view 3170 and a sectioned side view 3175 is presented. A bottom view 3180 is also presented. Importantly, the first and second contours that mate with the user's nasion are retained.

Figure 24:
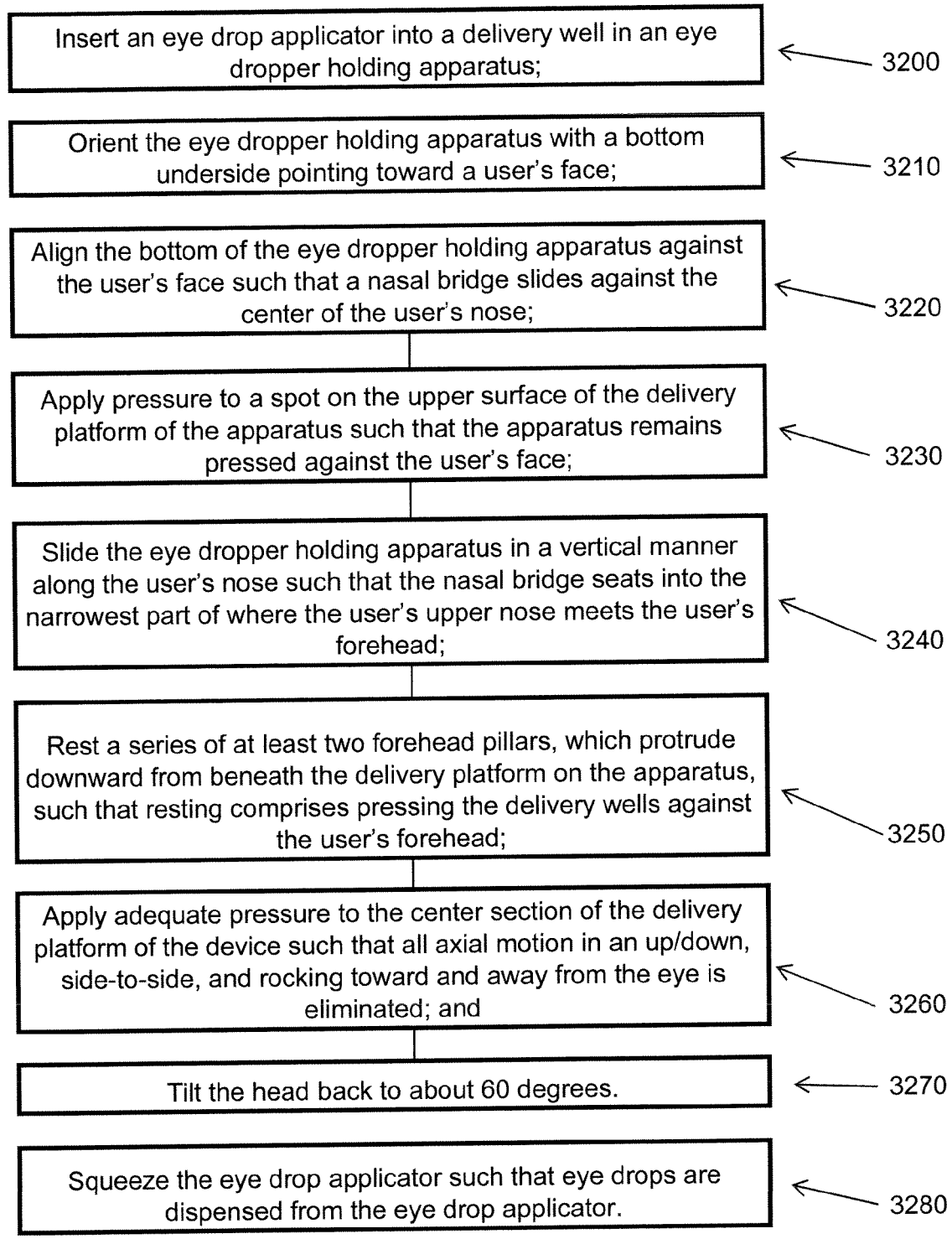
FIG. 24 is a method of using the eye dropper holder device.

Referring now to FIG. 24, the method of using the device to apply eye drops is comprised of the following steps. First, the user inserts an eye drop application apparatus 3200, such as a bottle of eye drops or an eye dropper, into one or both of the delivery wells. The user then orients 3210 the eye dropper holding apparatus with a bottom underside pointing toward a user's face and with the eye drop supply on the side opposite the user's face side. The user then aligns 3220 the bottom of the eye dropper holding apparatus against the face so that a nasal bridge slides against the center of the user's nose and applies pressure 3230 to a spot on the center of the upper surface of the delivery platform of the apparatus such that the apparatus remains pressed against the user's face. The user then slides 3240 the eye dropper holding apparatus in a vertical manner along the user's nose such that the nasal bridge eventually automatically seats into the narrowest part of the user's nasion, where the user's upper nose meets the user's forehead. The user also rests 3250 the series of at least two forehead pillars, which protrude downward from beneath the delivery platform on the apparatus onto the user's forehead. The user should apply adequate pressure 3260 to the center section of the delivery platform of the device such that all axial motion in an up/down, side-to-side, and rocking toward and away from the eye is eliminated. The user should tilt the head back 3270 so that the optimal angle between the user's head and the horizon is about 60 degrees. The user finally squeezes the eye drop applicator 3280 such that eye drops are dispensed from the eye drop applicator. The user may repeat this step as many times as necessary. The user may also perform these steps in an order different from the order described here, such as tilt the head back at a 60 degree angle as the first step or in between any of the two steps mentioned herein.

Figure 25:
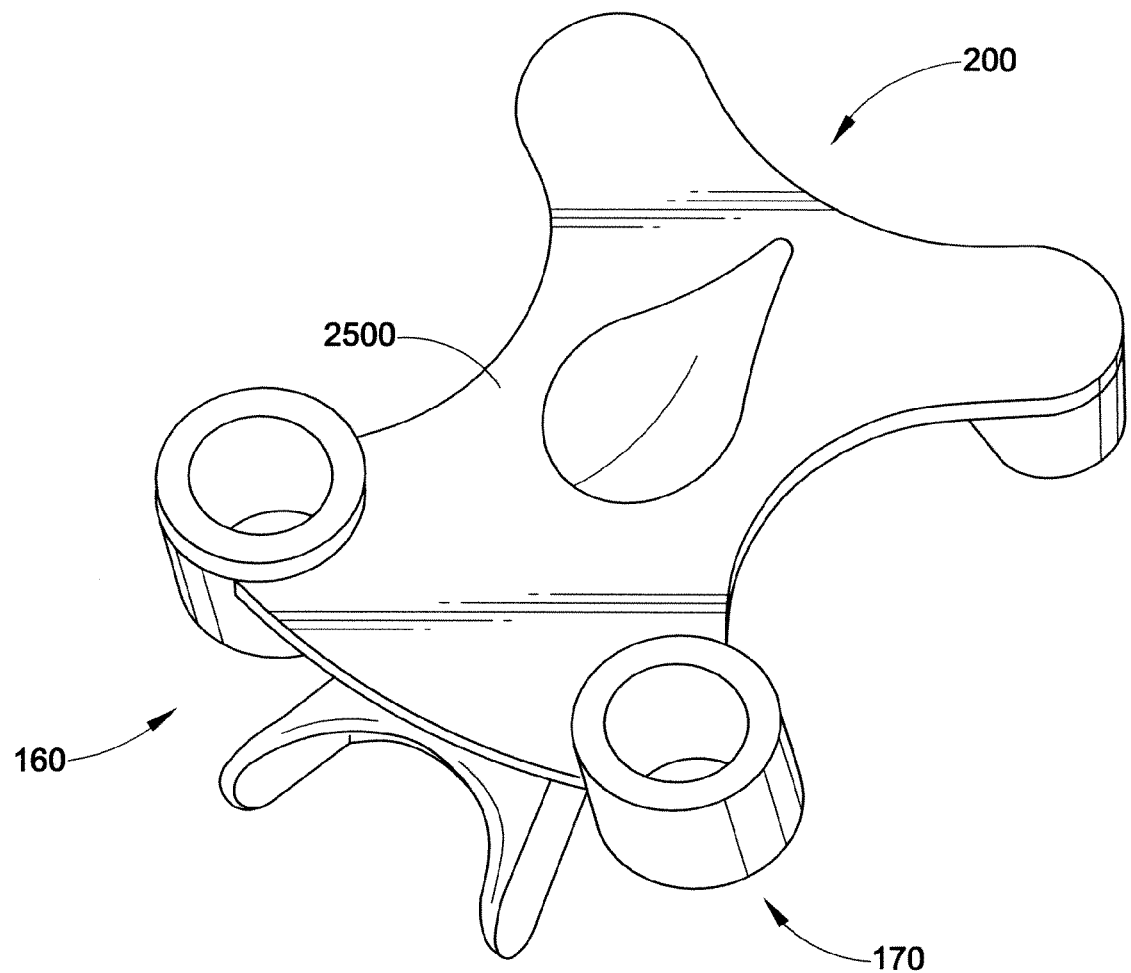
FIG. 25 illustrates a wider and tapered delivery well viewed from above the surface of the device.

Referring now to FIG. 25, the tapered delivery wells discussed in FIG. 15 and FIG. 16 are further illustrated from the upper surface of the delivery platform. The delivery wells 160, 170 in this embodiment are modified to taper, becoming narrower in diameter as the depth of the deliver well increases relative to the upper surface of the delivery platform 200. The top of the delivery well 160 begins at a height above 2500 the surface of the delivery platform 200. The portion of the delivery well 160 above the surface 2500 of the delivery platform 200 curves inward and then tapers downward 2440 as the depth of the delivery well increases. The outside outer cylinders of the delivery wells do not taper and remain a constant diameter.

Figure 26:
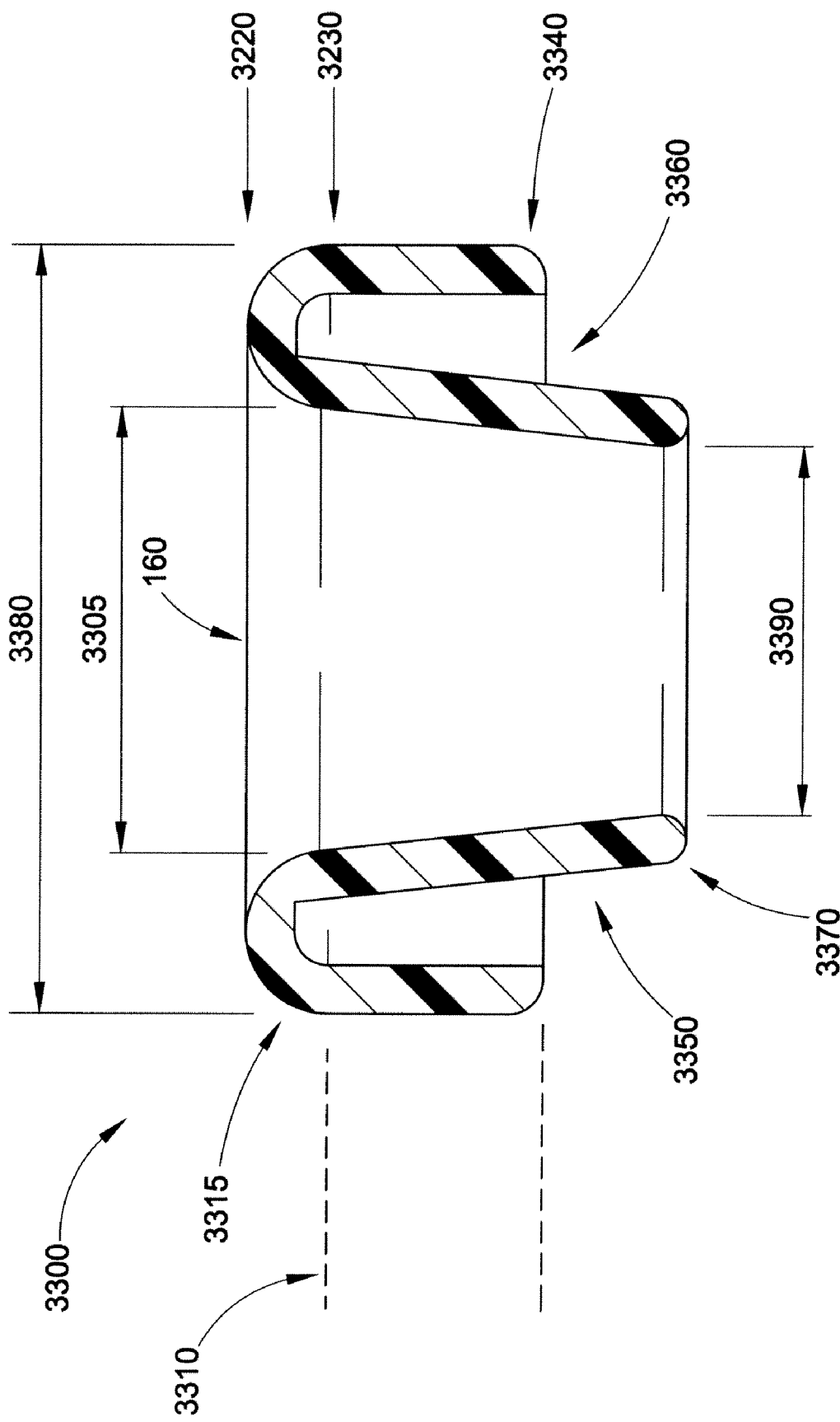
FIG. 26 illustrates a close-up, cross sectioned view of the delivery well from FIG. 11

FIG. 26 presents a close-up, cross sectioned view 3300 of an alternative embodiment of the delivery well 160 originally presented in FIG. 11, 1360, 1370. Here the delivery platform 3310 is shown in relation to the delivery well 160 such that a portion of the delivery well 3315 extends above the delivery platform 3310 at a distance between the top of the delivery well 3320 and the point where the delivery well intersects 3330 the delivery platform 3310. The delivery well 160 also extends and protrudes below 3350 the delivery platform 3310. The protruding side 3350 is the distance that the delivery well 160 extends from below the point where the bottom 3340 of the delivery platform 3310 intersects the delivery well 3340 to the bottom of the delivery well 3370. The side of the delivery well 3350 is not in contact with the delivery platform 3310 and the delivery platform 3310 is separated from the side of the delivery well 3350 by a hollow portion 3360. The top 3315 of the delivery well is at a diameter 3380 that exceeds the diameter of the open portion of the delivery well 3305. The sides 3350 of the delivery well 160 taper such that the bottom of the delivery well 3370 has a diameter 3390 smaller than the top diameter 3305 of the delivery well.

The exemplary embodiment has been described with reference to the preferred embodiments. Obviously, modifications and alterations will occur to others upon reading and understanding the preceding detailed description. It is intended that the exemplary embodiment be construed as including all such modifications and alterations insofar as they come within the scope of the appended claims or the equivalents thereof.

What is claimed is:

1. An eye dropper alignment apparatus comprising:
   a delivery platform with a front side, a back side, an upper edge and a lower edge;
   at least two supporting stabilizing forehead pillars extending from the back side of the delivery platform and located on corners of the delivery platform adjacent the upper edge;
   at least one delivery well opening to facilitate the insertion of an eye drop fluid dispenser, the depth wise dimension of the at least one delivery well directed away from the delivery platform and located in a corner of the delivery platform adjacent the lower edge; and
   a nasal bridge extending from the back side of the delivery platform, wherein the nasal bridge is in a plane parallel to the delivery platform, an arc of the nasal bridge being convexly contoured to dispose into a snug cradle position of engagement across the lowest point of a user's nasion, and ends of the nasal bridge disposed to straddle the width of a user's nose.

2. The apparatus of claim 1, wherein a distance from an axis bisecting the delivery platform into equal symmetric halves, to the center of the delivery well is the average distance between the center of a human nose and the corner of a human eye.

3. The apparatus of claim 1, wherein a distance from an axis bisecting the delivery platform into equal symmetric halves, to the center of the delivery well is the average distance between the center of a human nose and the center of a human eye.

4. The apparatus of claim 1, wherein the distance from the center of the delivery platform to the center of the delivery well is any distance between the center of a human nose and the outer corner of a human eye.

5. The apparatus of claim 1, wherein the distance from the center of the delivery platform to the center of the delivery well is within a range of from about 0.65 inches to about 1.64 inches.

6. The apparatus of claim 1, wherein the delivery well is movable for locating at variable distances away from the center of the delivery platform in an axis across the width of the eye.

7. The apparatus of claim 1, wherein the front side of the delivery platform is asymmetric relative to an apparatus center-line and contains at least two delivery wells located on the delivery platform.

8. The apparatus of claim 1, wherein the eye drop fluid dispenser is at least one of a bottle of eye drops and an eye dropper.

9. The apparatus of claim 1, wherein the edges of the delivery well are threaded to accommodate a screw capped eye drop fluid dispenser.

10. The apparatus of claim 1, wherein the delivery well further contains a movable, adjustable blade which enters the delivery well, applies a force against a side of the tip of the eye drop fluid dispenser, and pushes the tip of the eye dropper such that an opposite part of the eye dropper tip is pushed against the opposite side of the delivery well.

11. The apparatus of claim 1, wherein the delivery well enables the eye drop dispenser to be inserted, firmly retained, and swiveled such that the eye drop fluid dispenser may pivot such that the tip of the eye drop fluid dispenser applies eye drops at an oblique alignment off of a visual axis drawn from the retina to a point through the center of the pupil.

12. The apparatus of claim 1, wherein the nasal bridge has cantilevers which gradually blend into the shape of nose pads.

13. The apparatus of claim 12, wherein a holding spot on the delivery platform contains a tactile edge such that the tactile edge is perceivable to human touch.

14. The apparatus of claim 1, wherein the nasal bridge contains flexible nose pads.

15. The apparatus of claim 1, wherein the nasal bridge is mounted on a slider that moves the nasal bridge up and down a bottom surface of the delivery platform.

16. The apparatus of claim 1, further including a holding spot sized to facilitate a finger located on the front side of the delivery platform.

17. The apparatus of claim 1, wherein the apparatus is packaged with a bottle of eye drops.

18. The apparatus of claim 1, wherein the delivery well extends downward from the delivery platform toward the direction of the eyeball surface to form a nozzle cylinder.

19. The apparatus of claim 18, wherein the nozzle cylinder is calibrated to position the eye drop fluid dispenser at a distance greater than or equal to the length of an eyelash over and above the surface of the eye.

20. The apparatus of claim 18, wherein the nozzle cylinder shields the entire tip of the eye drop fluid dispenser.

21. The apparatus of claim 18, wherein the nozzle cylinder is tapered such that the delivery well has a greatest diameter on the surface of the top of the delivery platform and a smallest diameter at the bottom of the delivery well.

22. The apparatus of claim 18, wherein the delivery well is further comprised of two concentric forms: an inner conical cylinder comprised of an upper diameter larger than a lower diameter, which receives a tip of the eye drop fluid dispenser; and an outer, not tapered cylinder, of a consistent diameter, which protects the tip of an eye drop dispenser from being contaminated through contact with the user's eyelash.

23. The apparatus of claim 18, wherein the delivery well is further comprised of two concentric forms: an inner conical cylinder which receives a tip of the eye drop fluid dispenser; and an outer cylinder which protects the tip of the eye drop dispenser from being contaminated through contact with the user's eyelash.

24. The apparatus of claim 1, wherein the delivery well opening to facilitate the insertion of the eye drop fluid dispenser further comprises holding the eye drop fluid dispenser off of a visual axis drawn from the retina to a point through the center of the pupil.

25. The apparatus of claim 1 containing a rotating arm that conveys the delivery well to a position perpendicular to either side of the delivery platform.

26. The apparatus of claim 1, wherein a distance from the center of the delivery platform to the center of the delivery well is calibrated such that the eye drop falls on the medial canthus recess area of the eye.

27. The apparatus of claim 1, wherein the back side of the delivery platform further contains at least one off visual axis red dot.

28. The apparatus of claim 1, wherein a delivery platform contains at least one thru-hole focal point.

29. The apparatus of claim 1 including means for facilitating bilateral sequential administration.

30. The apparatus of claim 1, further including an imprint on the surface of the delivery platform illustrating how to use the apparatus.

31. The apparatus of claim 30, wherein the imprint is comprised of Braille dots.

* * * * *